United States Patent [19]

Gottstein

[11] 4,380,512

[45] Apr. 19, 1983

[54] 2β-CHLOROMETHYL-2α-METHYLPENAM-3α-CARBOXYLIC ACID SULFONE AND SALTS AND ESTERS THEREOF

[75] Inventor: William J. Gottstein, Fayetteville, N.Y.

[73] Assignee: Bristol-Myers Company, New York, N.Y.

[21] Appl. No.: 271,744

[22] Filed: Jun. 8, 1981

Related U.S. Application Data

[63] Continuation-in-part of Ser. No. 214,831, Dec. 11, 1980, abandoned, which is a continuation-in-part of Ser. No. 113,894, Jan. 21, 1980, abandoned.

[51] Int. Cl.³ ................. C07D 499/00; A61K 31/425
[52] U.S. Cl. .............................. 260/245.2 R; 424/270
[58] Field of Search .................. 260/245.2 R; 424/270

[56]  References Cited

U.S. PATENT DOCUMENTS

| 3,123,539 | 10/1978 | DiNinno | 424/270 |
| 4,058,521 | 11/1977 | Uyeo et al. | 260/239.1 |
| 4,180,506 | 12/1979 | Pratt | 424/270 |
| 4,234,579 | 11/1980 | Barth | 260/245.2 R |
| 4,342,772 | 8/1982 | Godtfredsen et al. | 424/271 |

Primary Examiner—Nicholas S. Rizzo
Attorney, Agent, or Firm—Herbert W. Taylor, Jr.

[57]  ABSTRACT

2β-Chloromethyl-2α-methylpenam-3α-carboxylic acid sulfone and salts and esters thereof were synthesized and found to be potent inhibitors of β-lactamases.

17 Claims, No Drawings

2β-CHLOROMETHYL-2α-METHYLPENAM-3α-CARBOXYLIC ACID SULFONE AND SALTS AND ESTERS THEREOF

CROSS-REFERENCE TO RELATED APPLICATIONS

This application is a continuation-in-part of my prior, copending application Ser. No. 214,831 filed Dec. 11, 1980 now abandoned which was in turn a continuation-in-part of my prior, copending application Ser. No. 113,894 filed Jan. 21, 1980 and now abandoned.

BACKGROUND OF THE INVENTION

1. Field of the Invention

The novel chemicals of the present invention include potassium 2β-chloromethyl-2α-methylpenam-3α-carboxylate sulfone which is useful as an inhibitor of β-lactamases.

2. Description of the Prior Art

The presumed association between the resistance shown by β-lactam antibiotics to certain bacteria and the ability of those bacteria to produce β-lactamases has led to an intensive search for β-lactamase inhibitors. Clavulanic acid is an example of such a compound presently under intensive study. Another β-lactamase inhibitor has in its acid form the structure

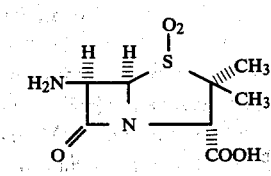

and is disclosed in European Patent Application No. 2927 published July 11, 1979.

The compound having the structure

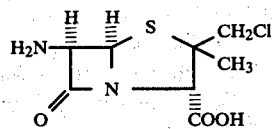

is disclosed in U.S. Pat. Nos. 4,036,847, 4,009,159, 3,993,646, 3,989,685 and 3,954,732.

For a corresponding sulfoxide having the 6-amino group acylated and, for example, the structure

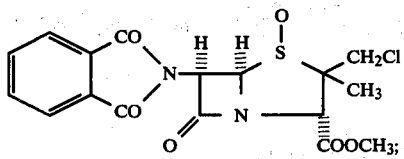

see Tetrahedron Letters, 38:3303-3310 (1975) and Kukolja et al., J. Org. Chem., 41, 2276-2279 (1976).

1,1-Dioxides of benzylpenicillin, phenoxymethylpenicillin and certain esters thereof have been disclosed in U.S. Pat. Nos. 3,197,466 and 3,536,698, and in an article by Guddal et al., Tetrahedron Letters, No. 9, 381 (1962). Harrison et al., in the Journal of the Chemical Society (London), Perkin I, 1772 (1976), have disclosed a variety of penicillin 1,1-dioxides, including methyl phthalimidopenicillanate 1,1-dioxide and methyl 6,6-dibromopenicillanate 1,1-dioxide. U.S. Pat. No. 3,544,581 discloses 6-aminopenicillanic acid 1-oxide.

For a brief review of esters of penicillins, see U.S. Pat. No. 3,996,236. Recent U.S. patents on esters of ampicillin and similar derivatives include U.S. Pat. Nos. 4,217,274, 4,081,546, 4,046,759, 4,036,829, 3,963,704, 3,954,735, 3,951,954, 3,941,774, 3,939,180, 3,931,150, 3,873,521, 3,860,579 and 3,697,507.

Recent U.S. patents on compounds (e.g. esters) or mixtures containing two like or unlike β-lactam derivatives include U.S. Pat. Nos. 4,181,659, 3,928,595, 3,869,449 and 3,867,538.

U.S. Pat. No. 4,155,912 describes 2-penem-3-carboxylic acid compounds having the formula

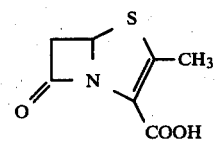

and esters and salts, and see also Farmdoc Abstracts 82090A, 10336B and 44337B.

The compound (under the number CP-45899) having the structure

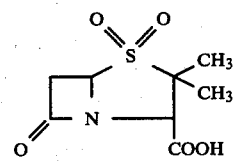

is an irreversibly acting β-lactamase inhibitor with excellent solution stability. It has weak antibacterial activity and potentiates the in vitro and in vivo activities of ampicillin versus β-lactamase-producing strains [A. R. English et al., Antimicrobial Agents and Chemotherapy, 14, 414–419 (1978), Aswapokee et al., J. Antibiotics 31(12), 1238–1244 (Dec. 1978) and Derwent's Farmdoc Abstracts 89627A and 73866B and U.S. Pat. No. 4,234,579].

Cignarella and associates [J. Org. Chem. 27, 2668 (1962)] reported the first deamination of 6-aminopenicillanic acid (6-APA) (1). When treated with sodium nitrite and hydrochloric acid, 6-APA was converted to 6-chloropenicillanic acid (96), isolated as the dibenzylethylenediamine salt. Substitution of hydrobromic acid in the reaction gave the 6-bromo derivative (97). Both deaminated products were devoid of microbiological activity against M. pyogenes aureus 209P.

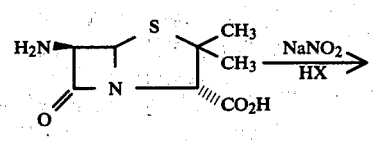

(1)

-continued

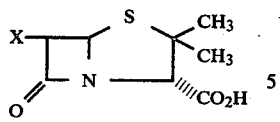

(96) X = Cl
(97) X = Br

Evrard and co-workers [Nature, 201, 1124 (1964)] prepared the methyl esters of (96) and (97) and showed that (97) could be hydrogenated to penicillanic acid (98). Their study emphasized the value of gas chromatography in the separation of penicillanates including methyl penicillanate (99).

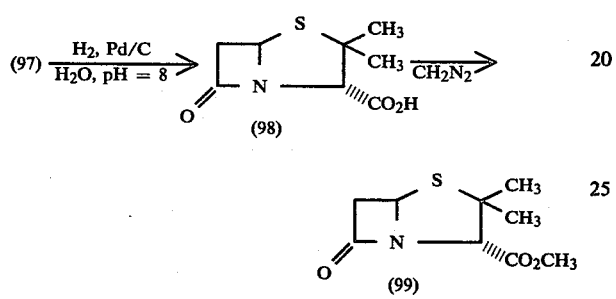

Compound 98 above is also described in U.K. No. 1,072,108 (1967).

6β-Bromopenicillanic acid is claimed in U.S. Pat. No. 4,180,506 and described as potentiating the in vitro activity of benzylpenicillin and ampicillin against certain bacteria.

According to U.S. Pat. Nos. 4,203,992 and 4,203,993 (2S,5R,6S)-6β-Bromo-3,3-dimethyl-7-oxo-4-thia-1-azabicyclo[3.2.0]heptane-2-carboxylic acid, S,S-dioxide, physiologically acceptable salts thereof and readily hydrolyzable ester thereof inhibit the action of the β-lactamase enzyme RTEM.

EPO No. 13,617 states that its invention relates to a process for the preparation of certain penicillin derivatives which are useful as β-lactamase inhibitors. The compounds which may be prepared by the process of this invention have formula (1), or a pharmaceutically acceptable salt or ester thereof:

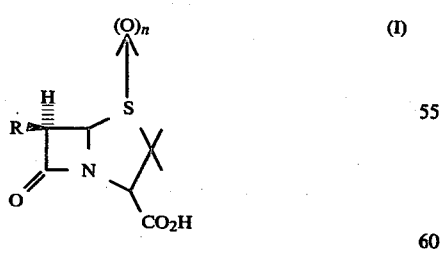

wherein R represents hydrogen, halogen, $C_{1-6}$alkylthio, $C_{1-6}$alkyl or alkyl substituted with phenyl, carboxy, $C_{1-6}$alkoxycarbonyl, hydroxy or $C_{1-6}$alkylthio, and n is zero, 1 or 2. In addition certain of the compounds produced by the process of the invention are novel compounds. Claim 1 therein reads as follows:

1. A compound of the formula (II):

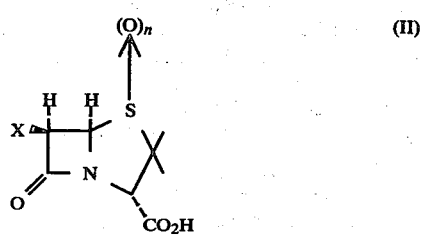

or a pharmaceutically acceptable salt or in-vivo hydrolysable ester thereof wherein X is a bromine or chlorine atom, and n is zero, 1 or 2, when substantially free from the corresponding 6α-substituted compound.

The compound (under the number of CP-45,899 and now known as sulbactam) having the structure

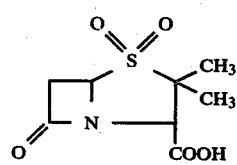

is an irreversibly acting β-lactamase inhibitor with excellent solution stability. It has weak antibacterial activity and potentiates the in vitro and in vivo activities of ampicillin versus β-lactamase-producing strains [see Derwent's Farmdoc Abstracts 89627A and 73866B].

It is disclosed by B. Baltzer et al., Mutual Pro-Drugs of β-Lactam Antibiotics and β-Lactamase Inhibitors, J. Antibiotics, 33(10), 1183–1192 (1980) that the principle of combining a β-lactam antibiotic with a β-lactamase inhibitor in a single molecule functioning as pro-drug for the two active components is illustrated by the linked esters 3 and 4 in which ampicillin and mecillinam, respectively, are combined with the β-lactamase inhibitor penicillanic acid sulfone. It is shown that in man these esters are excellently absorbed from the gastrointestinal tract and after absorption hydrolyzed with simultaneous liberation of the active components. As a result high blood and tissue levels of antibiotic and β-lactamase inhibitor in a balanced ratio are attained. The advantages of "mutual pro-drugs" over the simple combinations are discussed.

Esters 3 and 4 referred to therein have the structures

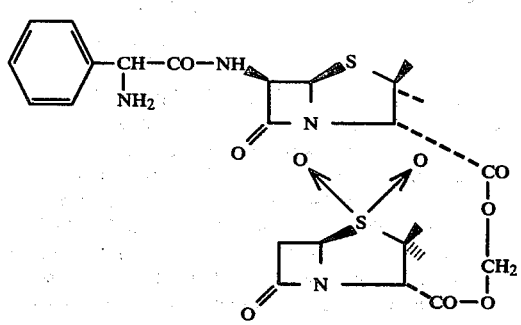

3

-continued

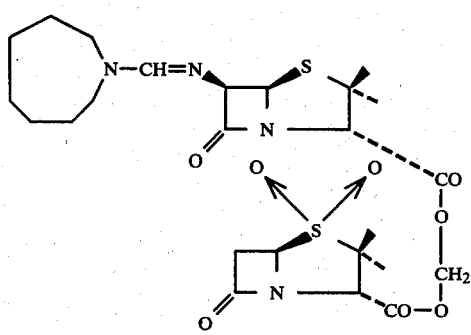

The following publications were discussed in the Baltzer et al. publication:

(1) Von Daehne, W.; E. Frederiksen, E. Gundersen, F. Lund, P. Morch, H. J. Petersen, K. Roholt, L. Tybring & W. O. Godtfredsen: Acyloxymethyl esters of ampicillin. J. Med. Chem. 13: 607–612, 1970

(2) Binderup, E.; W. P. Godtfredsen & K. Roholt: Orally active cephaloglycin esters. J. Antibiotics 24: 767–773, 1971

(3) Wheeler, W. J.; W. E. Wright, V. D. Line & J. A. Frogge: Orally active esters of cephalosporin antibiotics. Synthesis and biological properties of 7-(D-2-amino-2-phenylactamido)-3-[5-methyl-(1,3,4-thiadiazol-2-yl)thiomethyl]-3-cephem-4-carboxylic acid. J. Med. Chem. 20: 1159–1164, 1977

(4) Wheeler, W. J.; D. A. Preston, W. E. Wright, G. W. Huffman, H. E. Osborne & D. P. Howard: Orally active esters of cephalosporin antibiotics. 3. Synthesis and biological properties of aminoacyloxymethyl esters of 7-[D-(—)-mandelamino]-3-[[(1-methyl-1Htetrazol-5-yl)thio]methyl]-3-cephem-4-carboxylic acid. J. Med. Chem. 22: 657–661, 1979

(5) Wright, W. E.; W. J. Wheeler, V. D. Line, J. A. Frogge & D. R. Finley: Orally active esters of cephalosporin antibiotics. II. Synthesis and biological properties of the acetoxymethyl ester of cefamandole. J. Antibiotics 32: 1155–1160, 1979

(6) Roholt, K.: Pharmacokinetic studies with mecillinam and pivmecillinam. J. Antimicrob. Chemother. 3 (Suppl. B): 71–81 1977

(7) Foulds, G.; W. E. Barth, J. R. Bianchine, A. R. English, D. Girard, S. L. Hayes, M. M. O'Brien & P. Somani: Pharmacokinetics of CP-45,899 and pro-drug CP-47,904 in animals and humans. Current Chemother, & Infect. Disease 1980: 353, 1980

(8) Aswapokee, N. & H. C. Neu: A sulfone β-lactam compound which acts as a β-lactamase inhibitor. J. Antibiotics 31: 1238–1244, 1978

(9) Engberg-Pedersen, H: Empirical equation for pharmacokinetic analysis of drug serum levels after oral application. Antimicr. Agents & Chemoth. 6: 554–562, 1974

(10) Jordan, M. C.; J. B. De Maine & W. M. M. Kirby: Clinical pharmacology of pivampicillin as compared with ampicillin. Antimicr. Agents & Chemoth.- 1970: 438–441, 1971

(11) Godtfredsen, W. O.: U.S. Pat. No. 3,869,449, 1975

(12) Christensen, B. G. & W. J. Leanza: U.S. Pat. No. 3,931,150, 1976

(13) Evrard, E.; M. Claesen & H. Vanderhaeghe: Gas chromatography of penicillin and penicillanic acid esters. Nature 201: 1124–1125, 1964

(14) English, A. R.; J. A. Retsema, A. E. Girard, J. E. Lynch & W. E. Barth: GP-45, 899, a beta-lactamase inhibitor that extends the antibacterial spectrum of beta-lactam: Initial bacteriological characterization. Antimicro. Agents & Chemoth. 14: 414–419, 1978

It is stated in GB No. 2044255 published Oct. 15, 1980 that the invention therein relates to hitherto unknown compounds of the general formula 1:

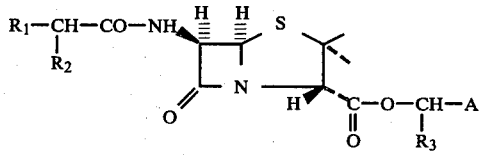

in which $R_1$ stands for a phenyl, 4-hydroxyphenyl, 1,4-cyclohexadienyl or 3-thienyl group; $R_2$ represents a primary amino or a carboxy group; $R_3$ is a hydrogen atom, or a lower alkyl, aryl or aralkyl radical, and A stands for a radical of a β-lactamase inhibitor containing a β-lactam ring as well as a carboxy group, A being connected via the carboxy group.

The new compounds are useful in the treatment of bacterial infections and are in particular strongly active against β-lactamase producing bacteria. See also Farmdoc abstracts 60773C and 60776C.

More recent specifications or patents issued or published on or after November, 1980 include the following:

U.S. Pat. No. 4,234,579 (Pfizer, Inc.—"Penicillanic Acid 1,1-Dioxides as β-Lactamase Inhibitors");

U.S. Pat. No. 4,244,951 (Pfizer, Inc.—"Bis-Esters of Methanediol with Penicillins and Penicillanic Acid 1,1-Dioxide");

GB No. 2,045,755A (Pfizer, Inc.—"Process and Intermediates for Penicillanic Acid 1,1-Dioxide and Esters Thereof");

GB No. 2,051,046A (Leo Pharmaceutical Products Ltd.—"Penicillanic Acid Derivatives");

GB No. 2,059,960A (Leo Pharmaceutical Products Ltd.—"Method for Producing Penicillanic Acid Derivatives").

SUMMARY OF THE INVENTION

The present invention provides the acid having the formula

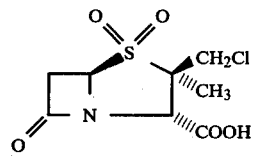

or a pharmaceutically acceptable salt of said acid or an easily hydrolyzed ester of said acid.

The pharmaceutically acceptable salts referred to above include nontoxic metallic salts such as sodium, potassium, calcium and magnesium, the ammonium salt and substituted ammonium salts, e.g. salts of such nontoxic amines as trialkylamines (e.g. triethylamine), procaine, dibenzylamine, N-benzyl-β-phenethylamine, 1-ephenamine, N,N'-dibenzyl-ethylenediamine, dehydroabietylamine, N,N'-bis(dehydroabietyl)ethylenediamine, N-(lower)alkylpiperidine (e.g. N-ethylpiperidine) and other amines which have been used to form pharmaceutically acceptable salts of pencillins and cephalosporins. The most preferred salts are the alkali metal salts, i.e. the sodium and potassium salts, and the ammonium salt.

As used herein the term "physiologically hydrolyzed esters" refers to those pharmaceutically acceptable esters known in the art to hydrolyze to the free acid form in vivo. Examples of suitable physiologically hydrolyzed esters include phenacyl, acetoxymethyl, pivaloyloxymethyl, α-acetoxyethyl, α-acetoxybenzyl, α-pivaloyloxyethyl, phthalidyl(3-phthalidyl), indanyl(5-indanyl), methoxymethyl, benzoyloxymethyl, α-ethylbutyryloxymethyl, propionyloxymethyl, valeryloxymethyl, isobutyryloxymethyl, 6-[(R)-2-amino-2-phenylacetamido]-3,3-dimethyl-7-oxo-4-thia-1-azabicyclo[3.2.0]heptane-2-carbonyloxymethyl and 6-[(R)-2-amino-2-p-hydroxyphenylacetamido]-3,3-dimethyl-7-oxo-4-thia-1-azabicyclo[3.2.0]heptane-2-carbonyloxymethyl and others for which the formulae are set forth below.

The preferred esters are the acetoxymethyl, pivaloyloxymethyl, methoxymethyl, phthalidyl, 5-indanyl, 6-[(R)-2-amino-2-phenylacetamido]-3,3-dimethyl-7-oxo-4-thia-1-azabicyclo[3.2.0]heptane-2-carbonyloxymethyl and 6-[(R)-2-amino-2-p-hydroxyphenylacetamido]-3,3-dimethyl-7-oxo-4-thia-1-azabicyclo[3.2.0]heptane-2-carbonyloxymethyl.

There is further provided by the present invention the process for the production as the desired product of the acid having the formula

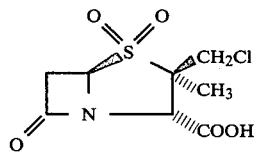

or a pharmaceutically acceptable salt of said acid which comprises the consecutive steps of (a) catalytically hydrogenating, as with a precious metal catalyst such as palladium, an ester having the formula

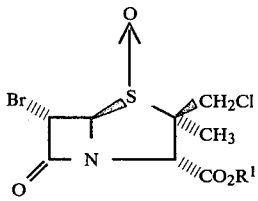

A wherein $R^1$ is benzyl or substituted benzyl and then (b) subjecting the hydrogenated product to oxidation to produce said desired acid or salt thereof and then, if desired, (c) esterifying said acid or salt thereof to produce an easily hydrolyzed ester of said acid.

There is further provided by the present invention the process for the production as the desired product of the acid having the formula

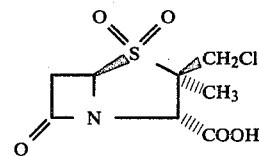

or a pharmaceutically acceptable salt of said acid which comprises the consecutive steps of (a) oxidizing, as with $KMnO_4$, $H_2O_2$ or like peroxide or peracid, an ester having the formula

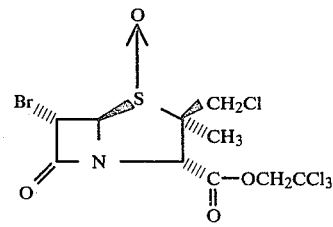

to produce an ester sulfoxide having the formula

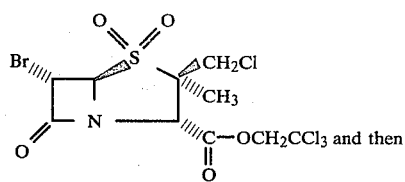

(b) reacting said ester sulfoxide (preferably in solution in an inert organic solvent and preferably in dimethylformamide) with a metal in acid, as with zinc in glacial acetic acid, at a temperature above 0° C. to produce said desired acid or salt and then, if desired, (c) esterifying said acid or salt thereof to produce an easily hydrolyzed ester of said acid.

A wide variety of oxidants known in the art for the oxidation of sulfides to sulfones can be used. However, particularly convenient reagents for alkali metal permanganates, e.g. potassium permanganate, and organic peracids, e.g. 3-chloroperbenzoic acid.

Particularly useful protecting groups for $R^1$ are the benzyl group and substituted benzyl groups, especially 4-nitrobenzyl. Benzyl and substituted benzyl groups can be removed conveniently by catalytic hydrogenation. In this case, a solution in an inert solvent of the compound of the formula A, wherein $R^1$ is benzyl or substituted benzyl, is stirred or shaken under an atmosphere of hydrogen, or hydrogen mixed with an inert diluent such as nitrogen or argon, in the presence of a catalytic amount of a hydrogenation catalyst. Convenient solvents for this hydrogenation are lower-alkanols, such as methanol; ethers, such as tetrahydrofuran and dioxan; low molecular weight esters, such as ethyl acetate and butyl acetate; water; and mixtures of these solvents. However, it is usual to choose conditions under which the starting material is soluble. The hydrogenation is usually carried out at a temperature in the range from about 0° to about 60° C. and at a pressure in the range from about 1 to about 100 kg./cm.$^2$. The catalysts used in this hydrogenation reaction are the type of agents known in the art for this kind of transformation, and typical examples are the noble metals, such as nickel, palladium, platinum and rhodium. The catalyst is usually present in an amount from about 0.01 to about 2.5 weight-percent, and preferably from about 0.1 to about 1.0 weight-percent, based on the compound of formula A. It is often convenient to suspend the catalyst on an inert support; a particularly convenient catalyst is palladium suspended on an inert support such as carbon. Additionally it is usual to buffer the reaction mixture in order to operate at a pH in the range from about 4 to 9, and preferably from 6 to 8. Borate and phosphate buffers are commonly used. The reaction typically takes about one hour.

There is further provided by the present invention the esters having the formula

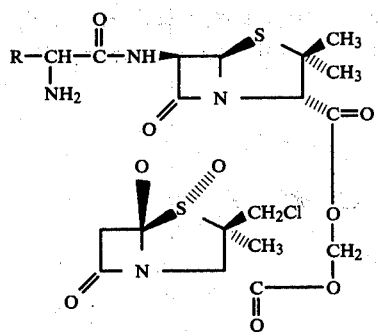

and

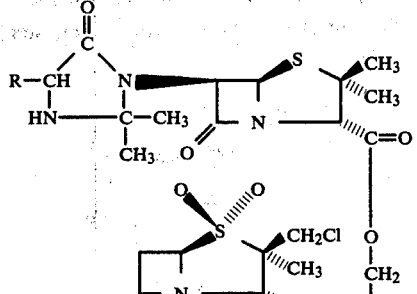

wherein R is 

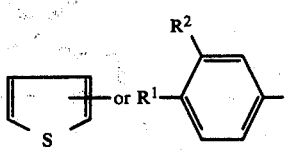

wherein $R^1$ is hydrogen or hydroxy and $R^2$ is hydrogen, hydroxy, methyl, methoxy or chloro and preferably the ester having the formula

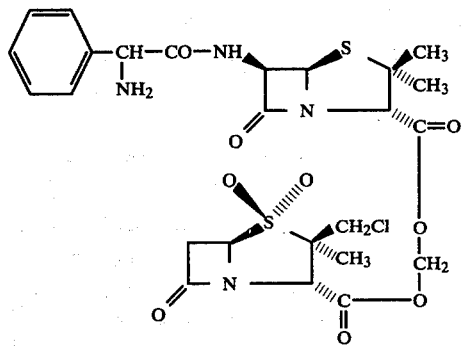

and the ester having the formula

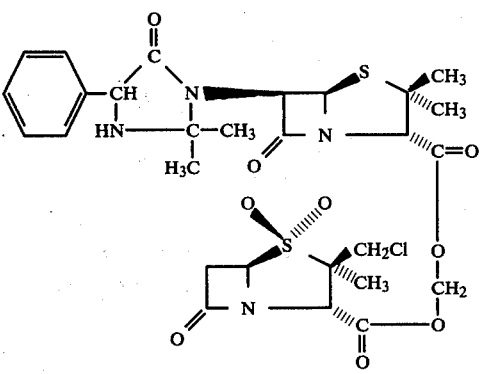

and the nontoxic, pharmaceutically acceptable acid addition salts of said esters and the process for producing such an ester of the former type which comprises the treatment with acid of a solution of a compound having the formula

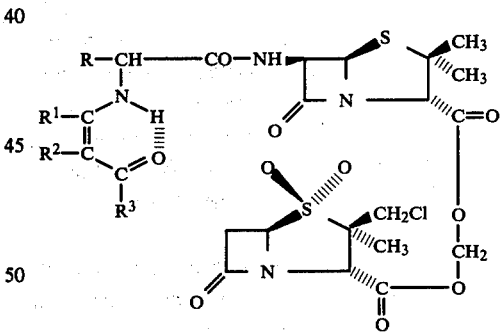

wherein R is 

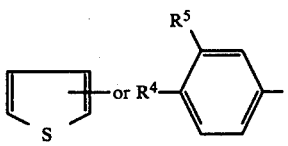

wherein $R^4$ is hydrogen or hydroxy and $R^5$ is hydrogen, hydroxy, methyl, methoxy or chloro and $R^1$ is alkyl, aralkyl or aryl, $R^2$ is hydrogen, alkyl, aralkyl or aryl and $R^3$ is alkyl, aralkyl, aryl, alkoxy, aralkoxy, aryloxy or

wherein R[4] and R[5] are each hydrogen, alkyl, aralkyl or aryl or, when taken together with the nitrogen atom, are piperidino or morpholino with said treatment with acid preferably being carried out in an organic solvent such as acetone or chloroform or in aqueous or partly aqueous solution and preferably between pH 1 and pH 5 at room temperature and the process for producing an ester of the latter type which comprises the reaction of a compound of the formula

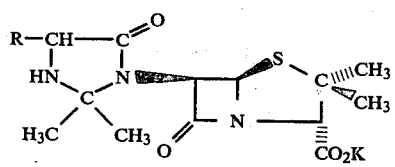

wherein R has the meaning set forth above with about an equimolar weight of the compound having the formula

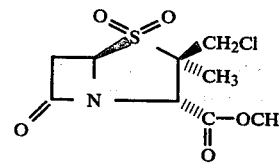

in an inert, anhydrous organic solvent, preferably dimethylformamide, at a low temperature, and preferably at about 0° C. to 10° C. until completion of the reaction.

It is further preferred that, in the amino-protecting group, R[1] is methyl, R[2] is hydrogen and R[3] is methoxy, ethoxy or methyl; this requires the use of methyl acetoacetate, ethyl acetoacetate or acetylacetone.

In the removal of the α-amino-protecting group it is preferred that use be made of a strong mineral acid such as hydrochloric acid or of formic acid.

There is further provided by the present invention as a novel intermediate an ester having the formula

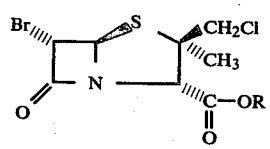

wherein R is benzyl or substituted benzyl, and preferably p-nitrobenzyl, and the process for its production which comprises heating, preferably at reflux, a compound having the formula

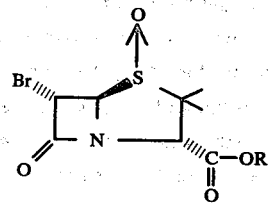

wherein R is benzyl or substituted benzyl and preferably p-nitrobenzyl, in an inert, anhydrous organic solvent, preferably dioxane, in the presence of large, and preferably equimolar, amounts of a weak tertiary amine, preferably quinoline, and an acid chloride, preferably benzoyl chloride, until the reaction is substantially complete.

There is provided by the present invention in addition as a novel intermediate an ester having the formula

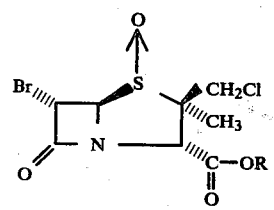

wherein R is benzyl or substituted benzyl, and preferably p-nitrobenzyl, and the process for its production which comprises oxidizing a solution in an inert solvent, preferably methylene chloride, of a compound having the formula

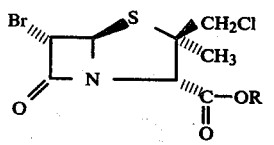

wherein R is benzyl or substituted benzyl, and preferably p-nitrobenzyl, at about room temperature by the use of a peracid, preferably m-chloroperoxybenzoic acid.

There is further provided by the present invention as a novel intermediate the ester having the formula

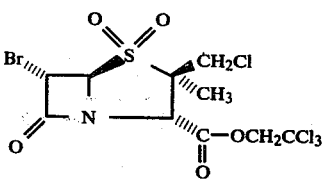

the process for its production which comprises oxidizing a solution in an inert solvent, preferably methylene chloride, of a compound having the formula

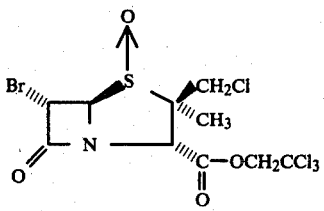

at about room temperature by the use of an oxidizing agent such as KMnO₄, H₂O₂ or like peroxide or, preferably a peracid, preferably m-chloroperoxybenzoic acid.

"Skellysolve B" is a petroleum ether fraction of b.p. 60°–68° C. consisting essentially of n-hexane ("Skellysolve" is a trade name of the Skelly Oil Co.).

The following examples are provided solely for the purpose of illustrating the preparation of representative compounds of the present invention and are not to be construed as limiting the invention.

EXAMPLE 1

Preparation of Potassium 2β-Chloromethyl-2α-methylpenam-3α-carboxylate Sulfone (BL-P2013)

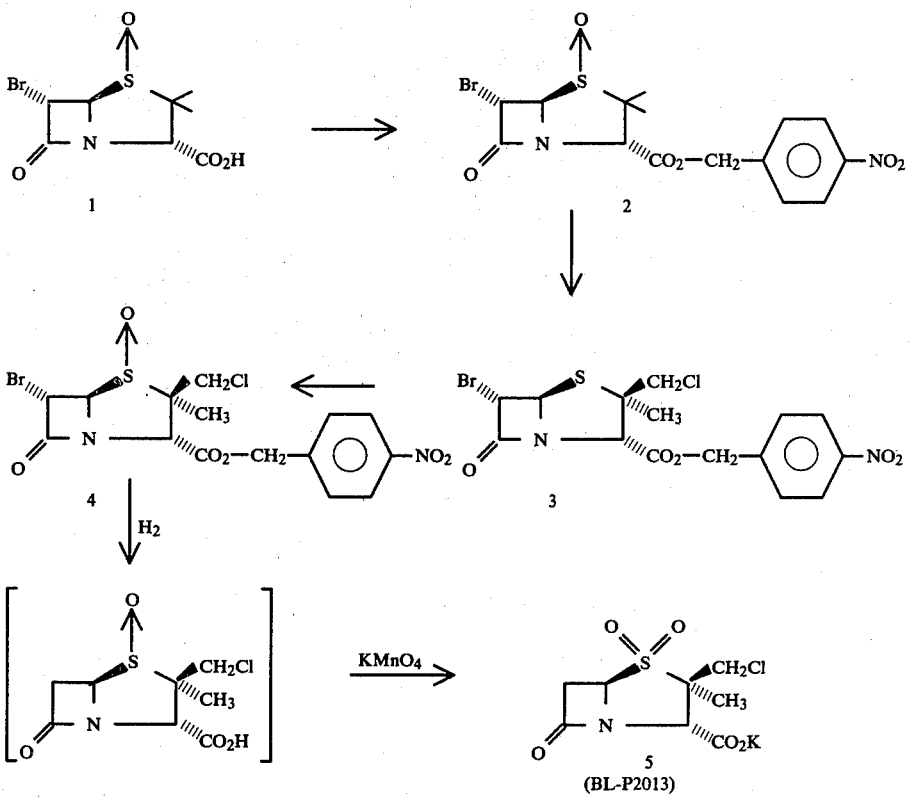

6α-Bromopenicillanic Acid S-Sulfoxide (1)

1. Dissolve 30 g (37.5 mmole) 6α-bromopenicillanic acid, N,N'-dibenzylethylenediamine salt [G. Cignarella et al., J. Org. Chem. 27, 2668 (1962) and E. Evrard, Nature 201, 1124 (1964)] in 330 ml of methylene chloride. Agitate and cool to 0° C.

2. Slowly add 13 ml (156 mmole) concentrated hydrochloric acid into the methylene chloride solution. The precipitation of dibenzylethylenediamine HCl salt (DBED.HCl) takes place within a minute. Stir the slurry at 0°–5° C. for 10 minutes.

3. Filter to remove the DBED.HCl precipitate through a precoated diatomaceous earth ("Dicalite") filter. Wash the cake with 150 ml of methylene chloride. The filtration should be completed as quickly as possible. Avoid holding the acidic methylene chloride solution for a prolonged period. There may be some filtration problems because of the fine nature of the precipitate. Addition of filter aid to the slurry may be helpful.

4. Wash the combined methylene chloride filtrates with 60 ml of cold water. Agitate 5 minutes and discard the aqueous phase. The pH of the wash is 2.0–2.3.

5. The methylene chloride solution containing 6α-bromopenicillanic acid is concentrated under reduced pressure to a volume of 65–80 ml. Cool and stir the solution to 5° C.

6. With vigorous agitation cautiously add 13 ml (86.9 mmoles) of 40% peracetic acid over a period of 30 minutes. The reaction is exothermic. Maintain temperature between 15°–18° C. with ice bath cooling. The sulfoxide begins to crystallize after 10 ml peracetic acid is added. Cool and stir the slurry at 0°–5° C. for two hours.

7. Filter and wash the snow white cake with the following sequence: 10 ml 5° C. water, then 10 ml 0°–5° C. methylene chloride, and finally wash with 15 ml of heptane.

8. Dry the cake in 45° C. air oven to constant weight, about 6–10 hours should be sufficient. Extended heating may generate a trace of pinkish color. The weight of 1 is about 16.26 gm, 73.24% yield.

9. The reaction mix and final product may be monitored by TLC using 15 toluene/4 acetone/1 acetic acid (HOAC) or 8 acetone/8 methanol/3 toluenel/HOAC solvent systems. The final product should be analyzed by NMR and IR.

p-Nitrobenzyl 6α-Bromopenicillanate S-Sulfoxide (2)

To a solution of 12 g (0.04 mole) of 6α-bromopenicillanic acid S-sulfoxide in 100 ml of acetone was added 7.5 g (0.041 mole) of potassium 2-ethylhexanoate. The salt was collected by filtration, washed with cold acetone and air dried to yield a total of 10 grams. The crystalline potassium salt was dissolved in 75 ml of dimethylacetamide and 7.8 g (0.04 mole) of p-nitrobenzyl bromide was added. The solution was stirred at 23° C. for 24 hours. The mixture was diluted with 500 ml of water and extracted with ethyl acetate. The ethyl acetate layer was washed four times with water and dried over anhydrous magnesium sulfate. The solvent was evaporated at 35° C. (15 mm) to an oil which crystallized. The light tan crystals of 2 were slurried with ether and collected by filtration to yield 9 g (70%) mp 124°-125° C. dec.

Anal. Calc'd for $C_{15}H_{15}BrN_2O_6S$: C, 41.98; H, 3.05; N, 6.52. Found: C, 42.00; H, 3.48; N, 6.98.

IR(KBr): 1800(s), 1740(s), 1610(w), 1520(s), 1450(m), 1350(s), 1060(m), 740(m) cm$^{-1}$. H-NMR (60 mHz, DMSO): δ1.22 (s,3H), 1.6 (s,3H), 4.67 (s,1H), 5.2 (d,J~1-5 Hz,1H), 5.45 (s,2H), 5.68 (d,J~1-5 Hz,1H), 7.5-8.5 (m,4H).

p-Nitrobenzyl 2β-Chloromethyl-2α-methyl-6-bromopenam-3α-carboxylate (3)

A solution of 5 g (0.012 mole) of p-nitrobenzyl 6α-bromopenicillanate S-sulfoxide (2) in 120 ml anhydrous dioxane was heated at reflux under nitrogen for 4 hours with 1.5 g (0.012 mole) of quinoline and 1.6 g (0.012 mole) of benzoyl chloride. The solution was diluted with 600 ml of water and extracted with ethyl acetate. The ethyl acetate extract was washed with 5% sodium bicarbonate solution, 5% phosphoric acid solution and finally with water. The organic layer was dried over anhydrous magnesium sulfate and evaporated to an oil at 35° C. (15 mm). The oil crystallized and was collected and washed with ether and then with cold toluene to yield 3, 3.5 g (65%) mp 130°-135° C. dec.

Anal. Calc'd for $C_{15}H_{15}ClBrN_2O_5S$: C, 40.06; H, 3.14; N, 6.23. Found: C, 40.19; H, 3.12; N, 6.75.

IR(KBr): 1792(s), 1740(s), 1610(w), 1520(s), 1353(s), 1280(m), 1025(w), 990(w), 750(w) cm$^{-1}$. NMR (60 mHz, DMSO): δ1.45 (s,3H), 3.5-4.3 (m,2H), 5.05 (s,1H), 5.42 (s,2H), 5.5(d,J~1.5 Hz,1H), 5.62 (d,J~1.5 Hz,1H), 7.5-8.5 (m,4H).

p-Nitrobenzyl 2β-Chloromethyl-2α-methylpenam-6α-carboxylate Sulfoxide (4)

A solution of 1 g (0.0022 mole) of p-nitrobenzyl 3β-chloromethyl-2α-methyl-6α-bromopenam-3α-carboxylate (3) dissolved in 50 ml of methylene chloride was stirred with 473 mg of (0.0022 mole) of m-chloroperoxybenzoic acid. The solution was stirred at 23° C. for 3 hours. The methylene chloride was evaporated to 20 ml at 15 mm and 33° C. and the concentrated solution was diluted with 50 ml of heptane ("Skellysolve B"). The solvent was decanted and the residue was slurried with ether and (4) soon crystallized; yield 250 mg, 24% mp 136°-137° C. dec.

Anal. Calc'd for $C_{15}H_{14}BrClN_2O_6S$: C, 38.68; H, 3.02; N, 6.02. Found: C, 39.14; H, 3.14; N, 3.13; N, 5.96.

IR(KBr): 1800(s), 1760(s), 1520(s), 1350(s), 1200(s), 1050(m), 830(w), 740(w) cm$^{-1}$. H-NMR (60 mHz, DMSO): δ 1.32 (s,3H), 3.8-4.5 (m,2H), 4.97 (s,1H), 5.25 (d,J~1.5 Hz,1H), 5.45 (s,2H), 5.6 (d,J~1.5 Hz,1H), 7.8-8.5 (m,4H).

Potassium 2β-Chloromethyl-2α-methylpenam-3α-carboxylate Sulfone (5) (BL-P2013)

To a solution of 7 g (0.015 mole) of p-nitrobenzyl 2β-chloromethyl-2α-methyl-6α-bromopenam-3α-carboxylate sulfoxide (4) in 150 ml of ethyl acetate was added a suspension of 4 g of 30% palladium on diatomaceous earth ("Celite") and 2.8 g of sodium bicarbonate in 150 ml of water. The mixture was hydrogenated for 3 hours at 50 psi. The catalyst was separated by filtration and the aqueous layer was separated and treated with 1.5 g of potassium permanganate in 50 ml of water. The mixture was stirred for 1 hour and 250 mg of sodium bisulfite was added. The mixture was filtered and the filtrate was adjusted to pH 2 with concentrated hydrochloric acid. The solution was lyophilized to give a white amorphous powder. The solid was extracted into ethyl acetate, evaporated to a volume of 20 ml and diluted with 100 ml of heptanes ("Skellysolve B"). White, hydroscopic, solid 2β-chloromethyl-2α-methylpenam-3α-carboxylic acid sulfone was collected. The acid was dissolved in acetone and treated with solid potassium 2-ethylhexanoate. A crystalline white salt precipitated to give, after collection by filtration, 170 mg of 5, mp>140° C. dec.

Anal. Calc'd for $C_8H_7ClKNO_5S.2H_2O$: C, 28.27; H, 3.24; N, 4.12. Found: C, 28.27; H, 3.69; N, 3.84.

IR(KBr): 1790(s), 1770(m), 1620(s), 1460(m), 1370(s), 1310(s), 1200(s), 1140(s), 955(m), 740(m) cm$^{-1}$. H-NMR (100 mHz, D$_2$O): δ1.68 (s,3H), 3.2-3.9 (m,J~2 Hz, J~4 Hz, J~6 Hz,2H), 4.0-4.4 (m,2H), 4.3 (s,1H), 5.02 (d d, J~4 Hz), J~2 Hz,1H).

EXAMPLE 2

Pivaloyloxymethyl 2β-Chloromethyl-2α-methylpenam-3α-carboxylate Sulfone

2β-Chloromethyl-2α-methylpenam-3α-carboxylic acid sulfone in dimethylformamide is treated with one equivalent of triethylamine and stirred to effect solution. Bromomethyl pivalate (1 equivalent) in dimethylformamide is then added. The resulting mixture is stirred at room temperature. The mixture is then clarified by filtration and the filtrate poured into ice water. The separated solid is collected by filtration, washed with water and dried to give the title ester.

The respective acetoxymethyl, methoxymethyl, acetonyl and phenacyl esters of the same acid are prepared by substituting in the method above for the bromomethyl pivalate used therein an equimolar weight of chloromethyl acetate, chloromethyl methyl ether, chloroacetone and phenacyl bromide, respectively.

EXAMPLE 3

Pivaloyloxymethyl
2β-Chloromethyl-2α-methylpenam-3α-carboxylate
Sulfone BL-P2024

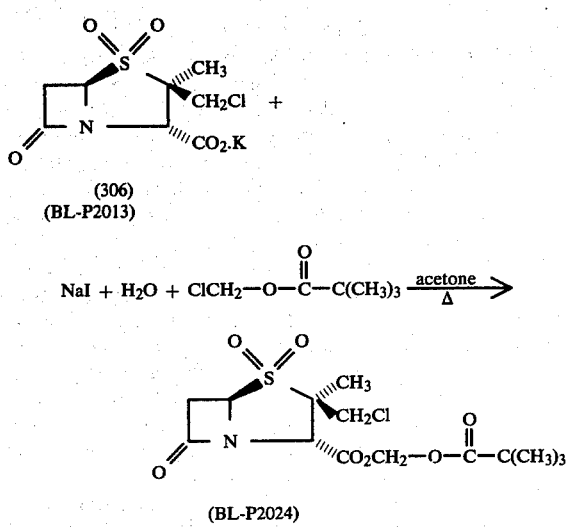

To a stirred suspension of 14.6 g (0.0487 mol) of BL-P2013 (5) in 200 ml of acetone was added 4 ml of a 10% aqueous solution of sodium iodide and the mixture was brought to reflux on the steam bath. To this refluxing suspension was added 14.8 ml (0.1 mol) of redistilled chloromethyl pivalate (B.P. 34° C. at 7 mm Hg) all at once. The mixture was stirred at reflux for three hours and then cooled to room temperature (22° C.). The crystalline solids were collected by filtration, washed with 3×30 ml of acetone and the combined filtrates were evaporated in an oil in vacuo at <22° C. The oil was then taken up in 500 ml of ethyl acetate and washed once with water (200 ml) and once with saturated $Na_2SO_4$ while being stirred with 2 g. of decolorizing carbon with cooling (ice bath). After 20 minutes the mixture was filtered through a diatomaceous earth (Dicalite) pad with suction and the pad was washed with 4×100 ml of ethyl acetate. The combined filtrates were concentrated in vacuo at 22° C. to an oil. The oil was then concentrated further at about 22° C. and <1 mm Hg to remove most of the residual chloromethyl pivalate. The remaining oil was then triturated twice with 50 ml portions of n-pentane and then left over the weekend in the cold room (about 10° C.) under n-pentane. The solid crystalline mass was then broken up to a solid powder under 40 ml of 4:1 mixture of ether-n-pentane. The product was then collected by filtration, washed with ether-pentane (1:1) then pentane and air dried. After drying in vacuo for four hours over $P_2O_5$ there was obtained 13.37 g. of pivaloyloxymethyl 2β-chloromethyl-2α-methylpenam-3α-carboxylate sulfone (about 75% yield) M.P. 93°–95° C.

Anal. Calcd. for $C_{14}H_{20}ClNO_7S$: C, 44.03; H, 5.27; N, 3.67. Found: C, 44.11; H, 5.08; N, 3.85.

EXAMPLE 4

Recrystallization of Potassium
2β-Chloromethyl-2α-methylpenam-3α-carboxylate
Sulfone (BL-P2013)

To a mixture of 20 ml of n-butanol and one gram of BL-P2013 (5) was added water, one ml at a time, with shaking in a separatory funnel until a pale yellow solution was obtained. The clear solution was filtered through a fluted filter paper and the flask and filter paper washed with about 10 ml of 9:1 n-butanol-$H_2O$ and the combined filtrates were diluted with a further 20 ml of n-butanol. The resulting solution was placed in a round-bottomed flask on the roto-vap and evaporated under reduced pressure to approximately one half the original volume. The snow white crystalline product was collected by filtration, washed with 6×10 ml of acetone and air dried. Yield 810 mg. After vacuum drying 6 hours over $P_2O_5$ at <1 mm Hg. there was obtained 800 mg M.P. 215° C. (dec.) (80% yield).

Anal. Calcd. for $C_8H_9ClNO_5SK.1H_2O$: C, 29.67; H, 3.39; N, 4.63; Cl, 10.94; K.F.$H_2O$, 5.56. Found: C, 29.23; H, 3.38; N, 4.49; Cl, 10.74; K.F.$H_2O$, 5.74.

This recrystallization procedure produces a crystalline monohydrate differing from the starting material which is essentially anhydrous.

EXAMPLE 5

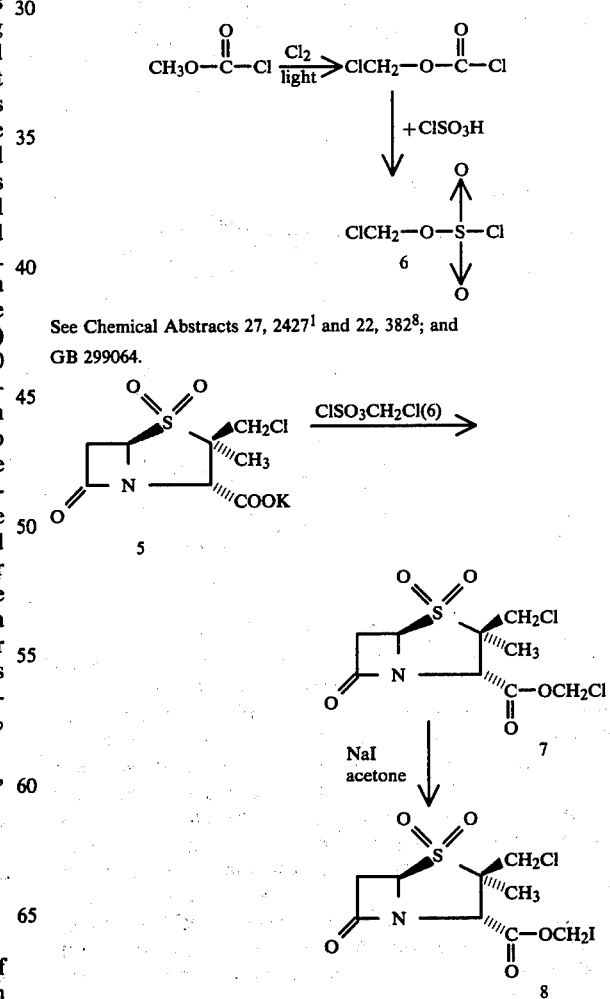

See Chemical Abstracts 27, 2427[1] and 22, 382[8]; and GB 299064.

-continued

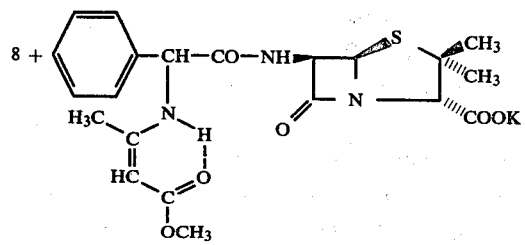

9(U.S. Pat. No. 3,316,247)

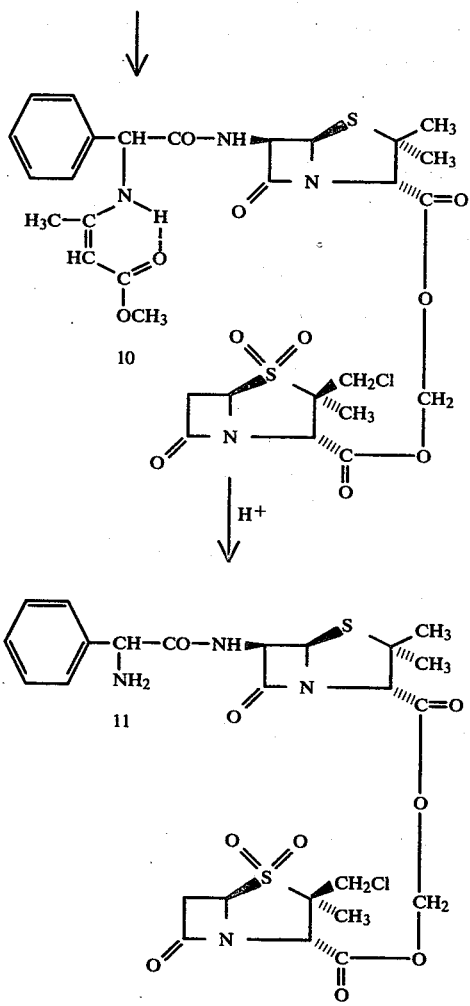

(a) A solution of chloromethyl chlorosulfate (0.115 mol) in 40 ml. dichloromethane is added dropwise, keeping the reaction temperature below 30° C., to a solution of compound 5 (0.1 mol) and potassium bicarbonate (0.3 mol) and tetrabutylammonium hydrogen sulfate (0.01 mol) in 200 ml. dichloromethane-water (1:1). At the end of the addition the mixture is stirred at room temperature for 30 minutes, the organic phase is separated and the aqueous phase is extracted with dichloromethane (50 ml.). The combined organic phases are dried ($Na_2SO_4$) and evaporated in vacuo to give a residue which is dissolved in ether (150 ml.). Insoluble material is filtered off after adding diatomaceous earth and the filtrate is evaporated in vacuo to provide compound 7.

(b) To a suspension of compound 5 (1.5 g.) in dimethylformamide (12 ml.) there is added 1.6 g. bischloromethyl sulfate and the mixture is stirred at room temperature for 45 minutes. After dilution with ethyl acetate (50 ml.) the mixture is washed with water and then aqueous sodium bicarbonate, dried and evaporated in vacuo to leave compound 7 as an oil.

(c) To a solution of compound 5 (0.005 mol) in dimethylformamide (7.5 ml.) there is added triethylamine (0.007 mol) and chloroiodomethane (0.030 mol) and the mixture is stirred at room temperature for four hours. After dilution with ethyl acetate (30 ml.) the mixture is washed with water (3×10 ml.) followed by saturated aqueous sodium chloride (5 ml.), dried and evaporated in vacuo to leave compound 7 as an oil.

(d) To a mixture of compound 5 (0.15 mol) silver nitrate (0.15 mol) and silver oxide (7.5 g.) in acetonitrate (750 ml.) there is added chloroiodomethane (1.5 mol). After stirring for 48 hours at room temperature, the silver salts are filtered off and the filtrate is evaporated to dryness in vacuo. The residue is dissolved in ethyl acetate (200 ml.) and the solution is washed with saturated aqueous sodium chloride, filtered, dried and evaporated in vacuo to give compound 7.

Compound 7 and other intermediates and final products of the present invention are purified, if desired, by column chromatography, as on "Sephadex" LH20 using chloroform-hexane, 65:35 as the eluent for example or by silica gel chromatography, e.g. using Mallinckrodt CC-7 and hexane-ethyl acetate, 3:2 or ethyl acetatepetroleum ether, 8:2 or 7:3 or 1:9 or 15:85 or ethyl acetate-n-hexane, 4:6 or 3:1 hexane-ethyl acetate, 3:1 or 1:1 or 1:4 or cyclohexane-ethyl acetate, 1:1.

Thin layer chromatography is also useful. "Sephadex" is cross-linked dextran 2-(diethylamino) ethyl 2-[[2-(diethylamino)ethyl]diethylammonio]ethyl ether chloride hydrochloride epichlorhydrin (See Merck Index, Ninth Edition, item number 7337).

A solution of compound 7 (0.2 mol) and sodium iodide (0.3 mol) in acetone (150 ml.) is stirred at room temperature for 18 hours. The resulting suspension is cooled to about 0° C. and adjusted to about pH 7.2 by the addition of saturated aqueous sodium bicarbonate with stirring. After decolorizing by titration with 0.5 M aqueous sodium thiosulfate, water (150 ml.) is added dropwise to the stirred mixture to precipitate solid compound 8 which is collected by filtration, washed with acetone-water 1:1 (2×20 ml.), isopropanol (2×20 ml.) and ether (2×20 ml.) and dried.

Ampicillin is converted to compound 9 by the use of methyl acetoacetate in the procedures of U.S. Pat. No. 3,316,247. Then to a stirred solution of compound 9 (0.57 mol) in dimethylformamide (1 liter) there is added at 5° C. 0.5 mol of compound 8. After strirring for 15 minutes at 5° C. the reaction mixture is poured into an ice-cold mixture of ethyl acetate (4 liters) and saturated aqueous calcium chloride (2 liters) with stirring. The organic layer is separated, washed with saturated aqueous calcium chloride (2×500 ml.), filtered and evaporated to about one liter in vacuo to provide a concentrated solution of compound 10. To this concentrate there is added water (500 ml.) and n-butanol (500 ml.) and then, dropwise, 4 N hydrochloric acid with stirring until the amino-protecting group is removed to provide a solution of compound 11. After the addition of the acid is finished ether (1 liter) and water (500 ml.) are added to the stirred mixture, the aqueous phase is separated and the organic phase is extracted with water (800 ml.). The combined aqueous extracts are washed with ether (1 liter) and then sodium chloride (640 g.) and dichloromethane (2 liters) are added and the mixture is stirred for 15 minutes. The organic phase is separated and the aqueous phase is extracted with dichloromethane (1 liter) and the combined organic extracts are dried (MgSO4) and evaporated to about 600 ml. under reduced pressure to give a concentrated solution of compound 11. Addition to the concentrate of 200 ml. 2-butanone followed by cooling precipitates solid 6-[(R)-2-Amino-2-phenylacetamido]-3,3-dimethyl-7-oxo-4-thia-1-azabicyclo[3.2.0]heptane-2-carbonyloxymethyl 2β-chloromethyl-2-α-methylpenam-3α-carboxylate sulfone (11) which is collected by filtration.

EXAMPLE 6

6-[(R)-2-Amino-2-p-hydroxyphenylacetamido]-3,3-dimethyl-7-oxo-4-thia-1-azabicyclo[3.2.0]heptane-2-carbonyloxymethyl 2β-chloromethyl-2-α-methylpenam-3α-carboxylate sulfone having the formula

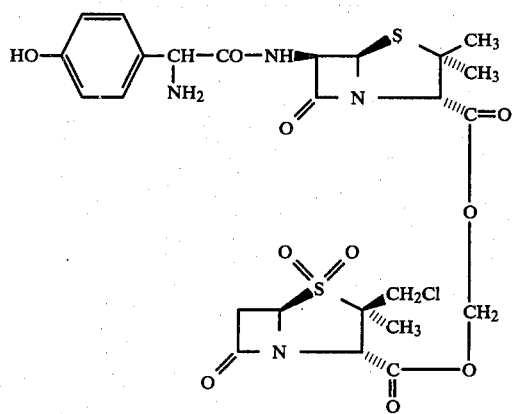

is produced by substituting amoxicillin for the ampicillin used in the procedure of Example 5.

EXAMPLE 7

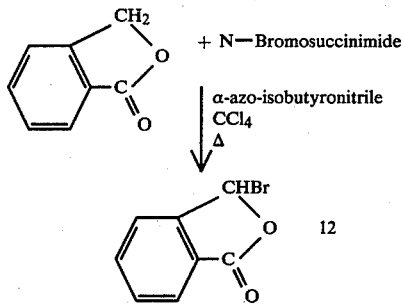

As taught by U.S. Pat. No. 3,860,579, recrystallized phthalide (50 g., 0.375 mol) and recrystallized N-bromosuccinimide (0.375 mol) were refluxed 4.5 hours in the presence of about 100 mgm α-azobutyronitrile in one liter CCl4. The mixture was cooled to about 15° C. and filtered to remove succinimide which was itself washed with about 100 ml. CCl4 and filtered. The combined CCl4 phases were concentrated in vacuo to about 150 ml. giving solid 3-bromophthalide which was collected by filtration, washed with about 50 ml. CCl4 and air-dried to yield 54 g. which weighed 50 g. after recrystallization from boiling cyclohexane, m.p. 84°–86° C.

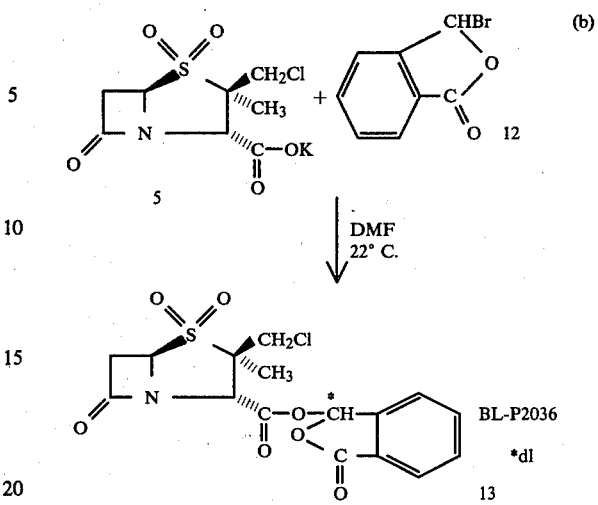

To a stirred partial solution and partial suspension of compound 5 (BL-P2013; 2.3 g., 0.0075 mol) in 20 ml. dimethylformamide (DMF; dried at least 3 weeks over 3A° molecular sieves was added 1.7 g. (0.008 mol) of 3-bromophthalide (12) and the mixture was stirred for 4 hours at 22° C. The resulting mixture was poured into a mixture of 200 ml. ice-cold water and 200 ml. ice-cold ethyl acetate (rinsing the flask with a little ethyl acetate) and the mixture was shaken. Then the organic solvent phase was separated and washed with seven portions of ice-cold water (100 ml.). The ethyl acetate phase was washed once with saturated aqueous Na2SO4, dried in the cold over Na2SO4, filtered and evaporated to dryness in vacuo to leave as the residue an oil which was triturated twice with methylcyclohexane (25 ml.), twice with "Skellysolve B" (b.p. 60°–68° C., essentially n-hexane) (25 ml.) and four times with 25 ml. n-hexane to 2.5 g. compound 13 as a nearly white solid after drying in air. This product was then dried over P2O5 at less than 1 mm Hg to give 2.5 g. compound 13, m.p. 104° C. (dec.). Its estimated purity was 85–95%.

Anal. Calcd. for $C_{16}H_{14}ClNO_7S$: C, 51.61; H, 3.79; N, 3.77; Cl, 9.53. Found: C, 52.59; H, 4.67; N, 3.21; Cl, 7.73; K.F.H2O, 0.27.

EXAMPLE 8

Pivaloyloxymethyl 2β-Chloromethyl-2α-methylpenam-3α-carboxylate Sulfone

A mixture of 1 g. (0.0031 mole) of potassium 2β-chloromethyl-2α-methylpenam-3α-carboxylate sulfone hydrate and 1 g. of 3 A molecular sieves was stirred in 15 ml. of dimethylacetamide for 2 hours at 23°. To this mixture was added 470 mg. (0.0031 mole) of pivaloyloxymethyl chloride and the stirring was continued for 18 hours. The molecular seives were collected and the filtrate was diluted with 100 ml. of water and extracted with ethyl acetate. The ethyl acetate was washed nine times with water and dried over anhydrous magnesium sulfate. The solvent was removed at 30° (15 mm) to leave an oil which was chromatographed on silica using silicar CC-7 (methylene chloride 8, ethyl acetate 2) showing 1 spot Rf 0.5. The residue obtained crystallized from heptane ("Skellysolve B") to yield 100 mg. (M.P. 94°–95°) of pivaloyloxymethyl 2β-chloromethyl-2α-methylpenam-3α-carboxylate sulfone.

Anal. Calcd.: C, 44.03; H, 5.27; N, 3.67. Found: C, 44.20; H, 5.24; N, 3.63.

The NMR and IR spectra were consistent for structure:

EXAMPLE 9

Sodium 2β-Chloromethyl-2α-methylpenam-3α-carboxylate Sulfone

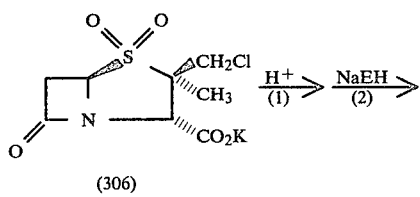

(306)

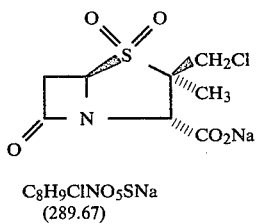

C$_8$H$_9$ClNO$_5$SNa
(289.67)

To a stirred solution of 500 mg. of BL-P2013 (potassium salt) in 5 ml. of H$_2$O and 10 ml. of ethyl acetate was added 2 N HCl until pH 1 was obtained (done in an ice-bath with vigorous stirring). The mixture was then saturated with Na$_2$SO$_4$, the aqueous layer separated and the organic phase dried briefly in ice over Na$_2$SO$_4$, filtered and treated dropwise with 50% NaEH (sodium 2-ethylhexanoate) in anhydrous n-butanol until neutral to moist pH paper. Product did not crystallize upon scratching and was then concentrated in vacuo to an oil which was dissolved in acetone (5 ml.), scratched—no crystals, ether added to cloud point—no crystals. Concentrated in vacuo on rotovap. to an oil which was dissolved in ethyl acetate—added one drop H$_2$O—scratched—no crystals. Concentrated in vacuo and then residue was triturated with 5 ml. of n-butanol—200 mg. of amorphous white powder obtained, ether washed—air dried—vacuum dried over P$_2$O$_5$ for 24 hours. 180 mg. final yield of sodium 2β-chloromethyl-2α-methylpenam-3α-carboxylate sulfone; dec. pt. >100° indef.

Anal. Calcd. for C$_8$H$_9$ClNO$_5$SNa: C, 33.10; H, 3.13; N, 4.89. Found: C, 33.20; H, 3.69; N, 4.44 K.F.H$_2$O, 4.04.

EXAMPLE 10

Potassium 2β-chloromethyl-2-methylpenam-3-carboxylate Sulfone (BL-P2013)

To 10 L of water, 130 g. (1.25 mole) of sodium hydrogen carbonate and 200 g. of 10% Pd on BaSO$_4$ were added 272 g. (0.565 mole) of p-nitrobenzyl 6α-bromo-2β-chloromethyl-2-methylpenam-3-carboxylate sulfone dissolved in 5 L of ethyl acetate. The mixture was hydrogenated at 40° C. and 1 Kg of pressure. After 5 hours, the hydrogen uptake became very slow and 200 g of 10% Pd on BaSO$_4$ were added and the mixture hydrogenated until no further significant hydrogen absorption was perceptible.

The slurry was filtered through a diatomaceous earth ("Celite") pad, the pad was washed with water and the aqueous phase washed with 3 L of ethyl acetate. To the aqueous solution, 3 L of ethyl acetate were added and the pH of the mixture adjusted to 1.5 with 150 ml of 12 N HCl at 10° C. The organic phase was separated and the aqueous solution saturated with Na$_2$SO$_4$.10 H$_2$O and extracted with 2×1 L of ethyl acetate. The combined extracts were dried with magnesium sulfate. The drying agent was removed and 260 ml of 2 N potassium 2-ethylhexanoate in butanol were added at 0° C.

After stirring 2 hours at 0° C., the potassium 2β-chloromethyl-2-methylpenam-3-carboxylate sulfone (BL-P2013) was collected and dried in a vacuum at room temperature.

Yield: 134.8 g (about 70%).

EXAMPLE 11 p-Nitrobenzyl 6α-Bromopenicillinate Sulfoxide

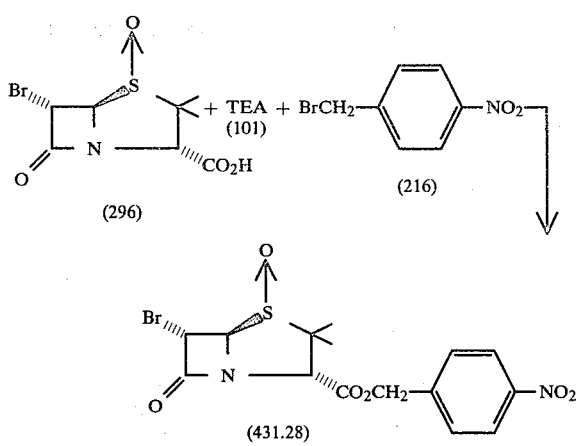

Procedure:

To 200 ml. of N,N-dimethylacetamide was added 44 g. (0.148 mole) of 6α-bromopenicillanic acid sulfoxide followed by 20.5 ml. (0.148 mole) of triethylamine and 38.2 g. (0.177 mole) of p-nitrobenzyl bromide. It was stirred at 22° for 20 hours.

The reaction mixture was poured into 1 liter H$_2$O and extracted into 3×300 ml. of methylene chloride. The combined methylene chloride extracts were washed with 200 ml. of 5% aqueous sodium bicarbonate solution and dried over sodium sulfate at 5° for half an hour. The solution was filtered and evaporated under vacuum to a residue. The residue was diluted with ether and the solid collected by filtration to yield 54 g. p-nitrobenzyl 6α-bromopenicillinate sulfoxide after drying.

85% yield.

Nmr consistent for structure.

The yield for this step was the same as for the K-salt esterification. The advantage is there was no need to make the K-salt. (A step which goes in 85% to 90% yield).

EXAMPLE 12

Preparation of p-Nitrobenzyl 6α-Bromopenicillanate Sulfoxide

To 4.375 L of N,N-dimethylacetamide was added 873.0 g (2.95 moles) of 6α-bromopenicillanic acid (S) sulfoxide and then with stirring and while keeping the internal temperature below 35° C., 293 g (2.95 moles) of triethylamine followed by 764 g (3.54 moles) of p-nitrobenzyl bromide. The mixture was stirred then at room temperature for 5 hours and let stand overnight.

The reaction mixture was poured into 20 L of water and extracted with 3×7 L of methylene chloride. The combined organic extracts were washed 5×7 L of water and then with 7 L of 5% aqueous sodium bicarbonate solution and dried over anhydrous magnesium sulfate.

The magnesium sulfate was filtered off and the solution evaporated to a crystalline residue; 4 L of diethyl ether were added and the crystals collected to yield after drying at room temperature 1171 g (92%) of p-nitrobenzyl 6α-bromopenicillanate sulfoxide.

Br 18.48% (calculated 18.53%), $\alpha_D$ (0.25% MeOH)+162°.

EXAMPLE 13

Preparation of p-Nitrobenzyl 6α-Bromo-2β-chloromethyl-2-methylpenam-3-carboxylate Sulfone To 16 L of acetic acid was added 364.6 g (0.812 mole) of p-nitrobenzyl 6α-bromo-2β-chloromethyl-2-methylpenam-3-carboxylate. To the solution so obtained and stirred at room temperature, a solution of 282 g (1.78 mole) of KMnO₄ in 26 L of water was added dropwise over 3 hours. The mixture was then stirred at room temperature for 1 hour and H₂O₂ (37%) was added dropwise until a colorless solution was obtained. 30 L of water were then added, the mixture stirred for 1 hour at room temperature and the crystalline precipitate was collected, washed with 3×5 L of water and with 2×2 L of ethanol and dried over vacuum at room temperature.

Yield: 297 g (76%).

$\alpha_D$ (0.5% CH₂Cl₂)+75.9°.

EXAMPLE 14

Preparation of BL-P2013 Free Acid

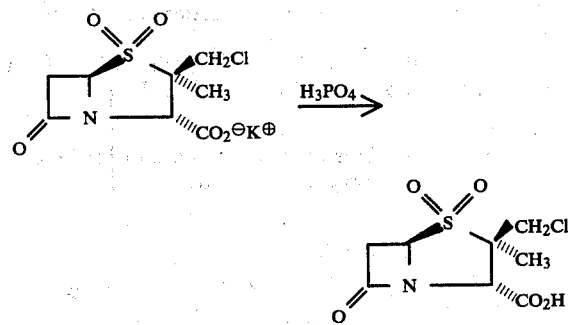

To a mixture of 25 ml of ethyl acetate and 10 ml of water was added 800 mg (0.00261 mole) of BL-P2013 potassium salt. After all of the solid had dissolved, the mixture was treated dropwise with 50% aqueous phosphoric acid with vigorous shaking until no more material precipitated from the aqueous layer. The ethyl acetate layer was separated, then washed with satuated sodium chloride solution and dried over anhydrous magnesium sulfate. The drying agent was removed by filtration and washed with 10 ml of ethyl acetate. (The wash solvent was combined with the original filtrate). "Skellysolve B" was then added to the ethyl acetate to the cloud point (approx. 10 ml). The mixture was treated with 500 mg of activated carbon ("Darko KB") and filtered. The filtrate was diluted with 15 ml of "Skellysolve B", then seeded with crystals of BL-P2013 free acid. After approx. 3 hours at room temperature, the crystalline precipitate of free acid was collected and dried in vacuo (15 min) over P₂O₅ to obtain 323 mg (46%) m.p. slow decomp. over 100°.

Anal. Calcd. for C₈H₁₀ClNO₅S: C, 35.89; H, 3.77; N, 5.23, Cl, 13.25. Found: C, 35.88, H, 3.91; N, 5.41; Cl, 13.52.

This product was found to be unstable when stored at 23° C. for seven days.

EXAMPLE 15

6α-Bromopenicillanic Acid Sulfoxide

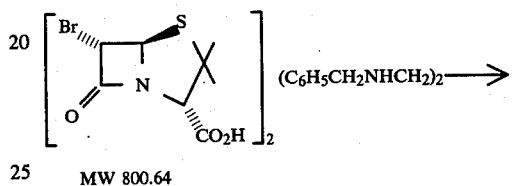

MW 800.64

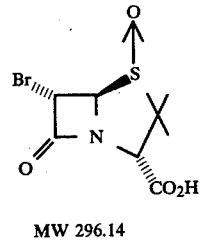

MW 296.14

To 3 l of methylene chloride was added 300 g (0.75 mole) of 6α-bromopenicillanic acid N,N'-dibenzylethylenediamine salt and this suspension was cooled to 5°. Then over a 15 min. period, with good stirring, 130 ml of conc. HCl was added dropwise. The slurry was stirred at 5° for 2 hours. It was then filtered through a ("Celite") pad of diatomaceous earth and the cake was washed with 3×250 ml of methylene chloride.

The combined methylene chloride solutions were washed with 2×500 ml H₂O and dried over sodium sulfate for 15 min. The sodium sulfate was removed by filtration and the filtrate evaporated under reduced pressure to approx. 750 ml.

This solution was cooled to 5° and, with vigorous stirring, 130 ml of 40% peracetic acid was added dropwise such that the temperature was maintained at 5° to 12°. The addition was quite exothermic. At the end of the addition, the slurry was stirred at 5° for 2 hours and the product collected by filtration and washed with 100 ml of cold H₂O (5°) and 100 ml of cold methylene chloride (5°). There was obtained 126 g (57%) of 6α-bromopenicillanic acid sulfoxide, m.p. 129°. The ir and nmr spectra were consistent for the desired product.

Anal. Calcd. for C₈H₁₀BrNO₄S: C, 32.44, H, 3.40; N, 4.73. Found: C, 32.30; H, 3.35; N, 4.71; H₂O, 2.18.

Potassium 6α-Bromopenicillanate Sulfoxide

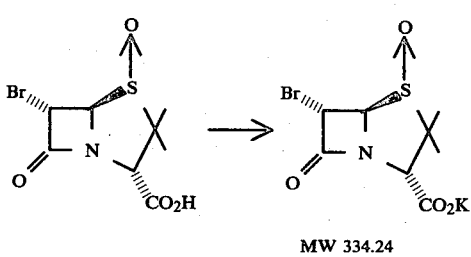

MW 334.24

To 3 l of acetone was added 126 g (0.43 mole) of 6α-bromopenicillanic acid sulfoxide and 162 ml of 50% by weight potassium 2-ethylhexanoate in n-butanol. After stirring 1 hour at 22°, the product was collected by filtration, washed with 2×250 ml of acetone and dried. There was obtained 127 g (90%) of potassium 6α-bromopenicillanate sulfoxide, m.p. 185°. The ir and nmr spectra were consistent for the desired structure.

Anal. Calcd. for $C_8H_9BrKNO_4S$: C, 28.75; H, 2.71; N, 4.19. Found: C, 29.03; H, 2.78; N, 4.04.

p-Nitrobenzyl 6α-Bromopenicillanate Sulfoxide

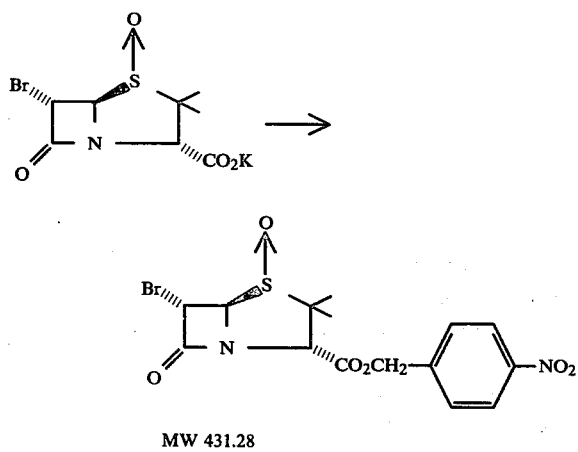

MW 431.28

To 1 l of N,N-dimethylacetamide was added 145 g (0.43 mole) potassium 6α-bromopenicillanate sulfoxide, and, with stirring, there was then added 115 g (0.53 mole) of p-nitrobenzyl bromide at 22°. The mixture was stirred at 22° for 20 hours.

The reaction mixture was poured into 3 l of $H_2O$ and extracted with 3×1500 ml of ethyl acetate. The combined ethyl acetate extracts were washed with 2×500 ml of 5% aqueous sodium bicarbonate solution and dried over sodium sulfate for ½ hour. The sodium sulfate was filtered off and the filtrate evaporated under reduced pressure to a residue to which 1 l of diethyl ether was added causing the product to crystallize. The crystals were collected by filtration, washed with 2×100 ml of diethyl ether and dried to yield 162 g (87%) of p-nitrobenzyl 6α-bromopenicillanate sulfoxide, m.p. 111°. The ir and nmr spectra were consistent for the desired structure.

Anal. Calcd. for $C_{15}H_{16}BrN_2O_6S$: C, 41.78; H, 3.51; N, 6.50. Found: C, 41.66; H, 3.45; N, 6.85; $H_2O$, 0.69.

p-Nitrobenzyl 6α-Bromo-2β-chloromethyl-2-methylpenam-3-carboxylate

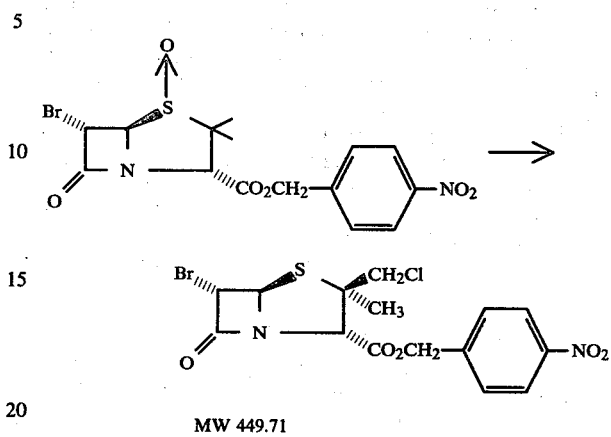

MW 449.71

To 1 l of p-dioxane was added to 70 g (0.16 mole) of p-nitrobenzyl 6α-bromopenicillanate sulfoxide followed by 21.2 ml (0.10 mole) of benzoyl chloride and 21.8 ml (0.19 mole) of quinoline. The reaction mixture was refluxed for 4 hours and then cooled to 22°, poured into 2500 ml of $H_2O$ and extracted into 3×800 ml of ethyl acetate. The combined ethyl acetate extracts were washed with 300 ml of 5% aqueous sodium bicarbonate solution, 300 ml of 5% aqueous phosphoric acid and 300 ml of $H_2O$. The ethyl acetate solution was dried over sodium sulfate for ½ hour and the sodium sulfate was removed by filtration. The filtrate was evaporated under reduced pressure to a residue which was redissolved in 1 l. of ethyl acetate and again evaporated under reduced pressure to a residue. Then 1 l. of diethyl ether was added and the product collected by filtration to yield 41 g (57%) of p-nitrobenzyl 6α-bromo-2β-chloromethyl-2-methylpenam-3-carboxylate, m.p. 132°. The ir and nmr spectra were consistent for the desired structure.

Anal. Calcd. for $C_{15}H_{14}BrClN_2O_5S$: C, 40.06; H, 3.14; N, 6.23. Found: C, 40.62; H, 3.11; N, 6.13.

p-Nitrobenzyl 6α-Bromo-2β-chloromethyl-2-methylpenam-3-carboxylate Sulfoxide

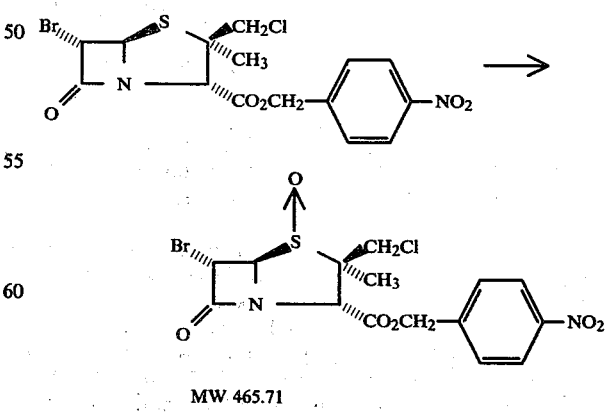

MW 465.71

To 1200 ml of methylene chloride was added 51 g (0.11 mole) of p-nitrobenzyl 6α-bromo-2β-chloromethyl-2-methlypenam-3-carboxylate followed by 23 g (0.12 mole) of m-chloroperoxybenzoic acid. The solution was stirred at 22° for 2 hours and evaporated under reduced pressure to a wet residue. The residue was stirred with 4 l of diethyl ether for 1 hour and allowed to stand at 10° for 20 hours. The product crystallized out and was collected by filtration, washed with 2×200 ml of diethyl ether and dried, yielding 39 g-nitrobenzyl 6α-bromo-2β-chloromethyl-2-methylpenam-3-carboxylate sulfoxide (75%), m.p. 132°. The ir and nmr spectra were consistent for the desired structure.

Anal. Calcd. for $C_{15}H_{14}BrClN_2O_6S$: C, 38.69; H, 3.03; N, 6.07. Found: C, 38.98; H, 3.04; N, 5.84; $H_2O$, 0.35.

Potassium
2β-Chloromethyl-2-methylpenam-3-carboxylate
Sulfone (BL-P2013)

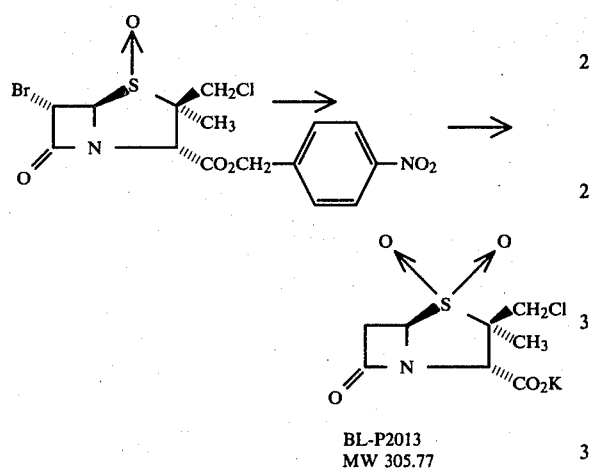

BL-P2013
MW 305.77

To 600 ml of $H_2O$ was added 8 g of 30% Pd on "Celite" and 16 g (0.19 mole) of sodium bicarbonate. Then 32 g (0.69 mole) of p-nitrobenzyl 6α-bromo-2β-chloromethyl-2-methylpenam-3-carboxylate sulfoxide was dissolved in 400 ml of ethyl acetate and added to the aqueous slurry. The mixture was hydrogenated on a Paar apparatus at 50 p.s.i. at 22° for 4 hours. The slurry was filtered through a thin "Celite" pad on a sintered glass funnel, the pad was washed with 2×50 ml $H_2O$ and the aqueous layer of the combined filtrate and washings was separated. The aqueous layer was washed with 200 ml of diethyl ether, then was cooled to 5° and, with stirring, a solution of 12 g. (0.076 mole) of $KMnO_4$ in 200 ml of $H_2O$ was added dropwise over a ½ hour period, keeping the pH between 7.5 and 8.0 by the addition of 40% $H_3PO_4$. When the pink color persisted for 5 minutes, no more $KMnO_4$ solution was added. The reaction mixture was stirred with a small amount (approx. 50 mg) of sodium bisulfite for ½ hour, and then the slurry was filtered through a "Celite" pad. The pad was washed with 2×50 ml of $H_2O$. The combined filtrate and washings were layered with 500 ml of ethyl acetate and, with stirring, the pH was adjusted to 1.5 by the addition of 2 N HCl. The layers were separated and the aqueous layer was saturated with sodium sulfate. It was reextracted with 2×400 ml of ethyl acetate and the combined ethyl acetate extracts were dried over sodium sulfate for ½ hour at 5°. The sodium sulfate was removed by filtration and the filtrate evaporated under reduced pressure to a residue. That residue was dissolved in 160 ml of acetone and 160 ml of diethyl ether and 50% by weight of potassium 2-ethylhexanoate in n-butanol was added until the solution was neutral to moist pH paper. The potassium salt of BL-P2013 crystallized out, was collected by filtration, washed with diethyl ether and dried. Yield 16 g potassium 2β-chloromethyl-2-methylpenam-3-carboxylate sulfone (BL-P2013) (76%), m.p. 202°. The ir and nmr spectra were consistent for the desired structure.

Anal. Calcd. for $C_8H_9ClKNO_5S$: C, 31.42; H, 2.97; N, 4.58. Found: C, 31.18; H, 2.98; N, 4.51; $H_2O$, 0.93.

EXAMPLE 16

Pivaloyloxymethyl
2β-Chloromethyl-2-methylpenam-3-carboxylate
Sulfone (BL-P2024)

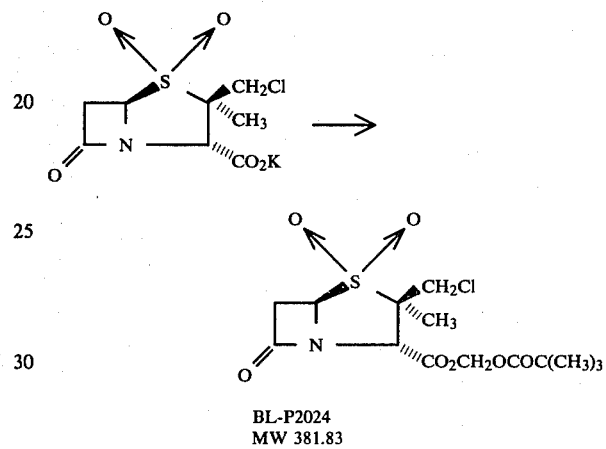

BL-P2024
MW 381.83

To a stirred suspension of 14.6 g (0.0487 mole) of potassium 2β-chloromethyl-2-methylpenam-3-carboxylate sulfone (BL-P2013) in 200 ml of acetone was added 4 ml of a 10% aqueous solution of sodium iodide and the mixture was brought to reflux on the steam bath. To this refluxing suspension was added 14.8 ml. (0.1 mole) of redistilled chloromethyl pivalate (bp 34° C. at 7 mm Hg) all at once. The mixture was stirred at reflux for three hours and then cooled to room temperature (22° C.). The crystalline solids were collected by filtration, washed with 3×30 ml of acetone and the combined filtrates were evaporated to an oil under reduced pressure at <22° C. The oil was then taken up in 500 ml of ethyl acetate and washed once with water (200 ml) and once with saturated $Na_2SO_4$ solution (200 ml). The solution was then dried briefly over $Na_2SO_4$ while being stirred with 2 g of decolorizing carbon with cooling (ice bath). After 20 min. the mixture was filtered through a "Celite" pad and the pad washed with 4×100 ml of ethyl acetate. The combined filtrates were concentrated under reduced pressure at 22° C. to an oil. The oil was then further concentrated at about 22° C. and <1 mm Hg to remove most of the residual chloromethyl pivalate. The remaining oil was then triturated twice with 50 ml portions of n-pentane and then left over the weekend at about 10° C. under n-pentane. The resulting solid crystalline mass was then broken up to a powder under 40 ml of a 4:1 mixture of diethyl ether-n-pentane. The product was then collected by filtration, washed with diethyl ether-n-pentane (1:1) then n-pentane and air dried. After drying under high vacuum for four hours over $P_2O_5$ there was obtained 13.37 g pivaloyloxymethyl 2β-chloromethyl-2-methylpenam-3- carboxylate sulfone (BL-P2024) about (75%), m.p. 93°-95° C.

Purification of BL-P2024

Approximately 3 g. of crude BL-P2024 (obtained as described above) was dissolved in 5 ml. of ethyl acetate, placed on a 4.5×40 cm. column of silica gel (Mallinckrodt CC-7), and eluted with 4:1 v/v $CH_2Cl_2$-ethyl acetate. The fractions containing a single spot at $R_f$ 0.84 (TLC on silica gel plates with 4:1 $CH_2Cl_2$-ethyl acetate, $I_2$ detection) were combined and concentrated under reduced pressure to 1.38 g. of a crystalline solid. A portion of this material (900 mg.) was dissolved in 5 ml. of ethyl acetate; the resulting solution was filtered, diluted almost to the cloud point with petroleum ether ("Skellysolve B") and then stored at room temperature for three days. The crystals which formed were collected by filtration, washed with petroleum ether and dried to give 560 mg., m.p. 100°-101°., of purified BL-P2024.

Anal. Calcd. for $C_{14}H_{20}ClNO_7S$: C, 44.03; H, 5.27; N, 3.67 Found: C, 44.11; H, 5.08; N, 3.85.

All temperatures in this application are given in degrees Centigrade.

EXAMPLE 17

Preparation of BL-P2013 Ammonium Salt

1. The free acid of BL-P2013 (250 mg.) dissolved in 20 ml. of acetone-methanol (1:1 by volume) was filtered to get a clear solution.

2. Anhydrous ammonium solution was prepared by adding 1 ml. of ammonium hydroxide (30%, reagent grade) to 10 ml. of acetone-methanol (1:1 by volume) solvent and then 1 gm. of anhydrous magnesium sulfate was added to that solution with mild agitation and the mixture was filtered through a filter paper; the filtrate was designated "anhydrous ammonium solution."

3. To the filtrate of Procedure 1, approximately 2 ml. of "anhydrous ammonium solution" was gradually added and mixed well.

4. A 100 ml. portion of diethyl ether was mixed with the mixture from Procedure 3 to precipitate the ammonium salt of BL-P2013.

5. The white ammonium salt was isolated from the solvent and washed with 2 portions of 50 ml. each of diethyl ether.

6. The isolated powder was dried at 35° C. vacuum oven for overnight.

7. Analytical data were as follows: Calculated % C 33.7; H 4.6; N 9.8;. Found: C 33.66; H 4.63; N 10.12; dry by KF. Microscopic Examination: crystalline substance.

EXAMPLE 18

Preparation of Non-hygroscopic Sodium Salt of BL-P2013

1. Dissolve 50 mg. of the free acid of BL-P2013 in 4 ml. of acetone-methanol (1:1 by volume) mixture. Filter to get a clear solution.

2. Prepare sodium 2-ethylhexanoate solution by dissolving 40 mg. of sodium 2-ethylhexanoate in 10 ml. of acetone-methanol (1:1 by volume) mixture.

3. To the filtrate of Procedure 1, add the 10 ml. solution of Procedure 2 and mix well.

4. A 10 ml. portion of diethyl ether was mixed with the mixture from Procedure 3 to precipitate the sodium salt of BL-P2013.

5. The white salt was immersed in the diethyl ether for 1-2 hours and then was isolated from the solvent and washed with 3 portions of 5 ml. each of diethyl ether.

6. The isolated powder was dried at 30° C. vacuum oven for overnight.

EXAMPLE 19

Recrystallization of BL-P2013

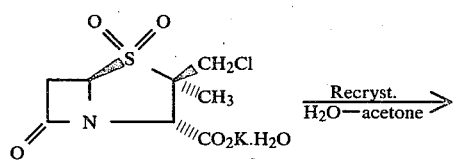

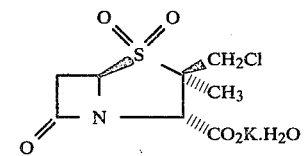

BL-P2013 (400 mg.) was dissolved in a minimum amount of acetone-$H_2O$ (1:1) by volume and diluted with 10 ml. of acetone, filtered, then diluted with acetone to about 25 ml., scratched, and after 30 minutes the crystalline hydrate was collected by filtration, washed well with acetone, air dried and then vacuum dried at <1 mm. Hg overnight.

Yield 280 mg.

Anal. Calcd. for $C_8H_9ClNOSK.H_2O$: C, 29.67; H, 3.39; N, 4.63; Cl, 10.94; $H_2O$, 5.55. Found: C, 29.32; H, 3.32; N, 4.44; Cl, 11.31; $H_2O$, 5.90.

EXAMPLE 20

N,N'-Dibenzylethylenediamine Salt of BL-P2013

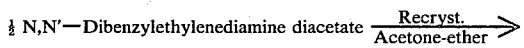

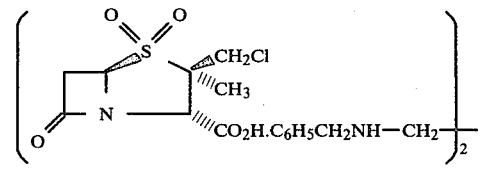

306 mg. (0.001 ml) of BL-P2013 was dissolved in 7 ml. $H_2O$ and added to a solution of 180 mg. (0.0005 mol) of N,N'-dibenzylethylenediamine diacetate in 7 ml. $H_2O$. The mixture was stirred and the salt crystallized and after stirring approximately 10-15 minutes the salt was collected by filtration and air dried to yield N,N'-dibenzylethylenediamine salt of BL-P2013 (300 mg). The material was recrystallized by dissolving it in approximately 10 ml. of boiling acetone and diluting with ether to the cloud point. 260 mg. of air dried and vacuum dried material was obtained.

Anal. Calcd: C, 51.69; H, 5.42; N, 7.53; Cl, 9.55. Found: C, 49.39; H, 5.49; N, 7.05; Cl, 8.96; $H_2O$, 1.23 (KF).

EXAMPLE 21

Chloromethyl Ester of BL-P2013

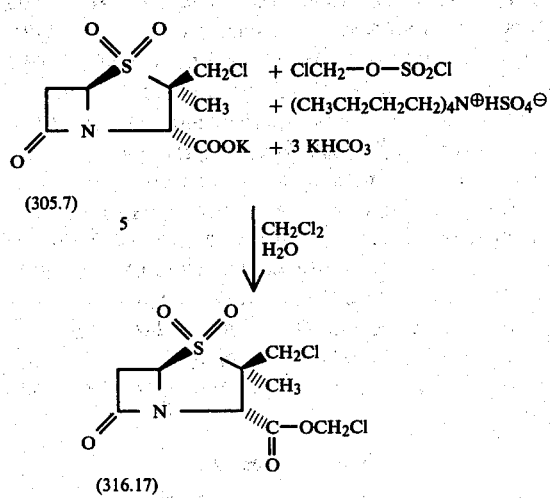

To a vigorously stirred mixture of 15.25 g (0.05 mol) of BL-P2013 (5), 15 g. (0.15 mol) KHCO$_3$ and 1.7 g (0.005 mol) of tetrabutylammonium hydrogen sulfate (Aldrich Chem. Co.) in a mixture of 50 ml. water and 50 ml. CH$_2$Cl$_2$ there was added dropwise a solution of 9.5 g (0.0575 mol) of ClCH$_2$-O-SO$_2$Cl in 40 ml. CH$_2$Cl$_2$. The temperature rose to 26° C. and after the addition (which took about 15 minutes) the mixture was stirred another 30 minutes. Because the product crystallized out more CH$_2$Cl$_2$ (about 400 ml.) was added to obtain a solution. The separated CH$_2$Cl$_2$ layer and a 50 ml. CH$_2$Cl$_2$ wash were combined, dried over MgSO$_4$ with stirring and 2 g of decolorizing carbon ("Darco KB") was added. After about 30 minutes the mixture was filtered, concentrated to about 50 ml. and isopropyl alcohol (150 ml.) was added. The rest of the CH$_2$Cl$_2$ was then removed under reduced pressure. The resulting crystalline precipitate was collected by filtration, washed well with isopropyl alcohol and air-dried. After vacuum drying at less than 1 mm. Hg there was obtained 8.5 of chloromethyl 2β-chloromethyl-2-methylpenam-3-carboxylate sulfone (7). M.p. 116° (dec., darkens above 100° C.).

Anal. Calcd. for C$_9$H$_{11}$Cl$_2$NO$_5$S: C, 34.18; H, 3.51; N, 4.43; Cl, 22.43. Found: C, 34.16; H, 3,45; N, 4.47; Cl, 22.46; H$_2$O, 0.33 (KF).

Estimated purity in the 90-95% range.

Iodomethyl Ester of BL-P2013

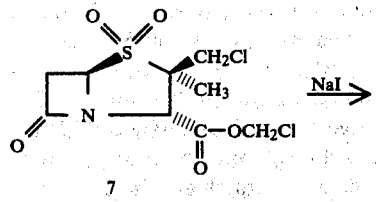

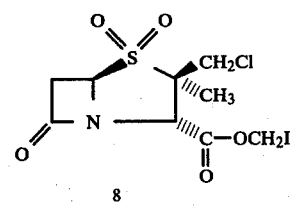

To a stirred mixture of 5 g. (0.0159 mol) of the chloromethyl ester of BL-P2013 (7) in 25 ml. acetone was added 3 g. (0.02 mol) of sodium iodide. The resulting slurry was stirred for 17 hours and then cooled to about 0° C. Two drops of saturated aqueous KHCO$_3$ were added and the mixture was slowly diluted dropwise with water over ten minutes until 50 ml. had been added. The slurry underwent a sudden color change from yellow to grey to purple to black and therefore the crystals were immediately collected by filtration and washed with cold acetone-water (1:2) and then isopropyl alcohol (3×10 ml), then diethyl ether and finally n-pentane and air-dried to yield 5.55 g. (91% yield) of the iodomethyl ester of BL-P2013 (8). M.p. 118°-119° C. with decomposition. Purity estimated at about 90%.

6-[(R)-2-Amino-2-phenylacetamido]-3,3-dimethyl-7-oxo-4-thia-1-azabicyclo[3.2.0]heptane-2-carbonyloxymethyl 2β-chloromethyl-2-α-methylpenam-3α-carboxylate sulfone (11)

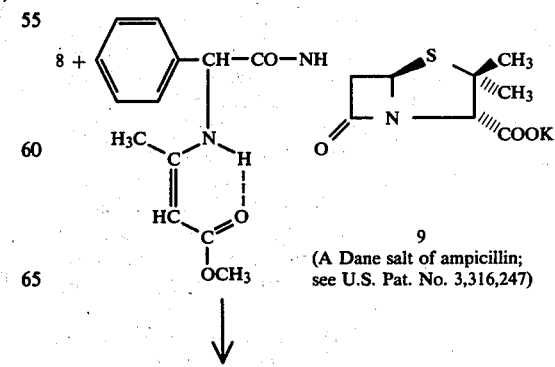

(A Dane salt of ampicillin; see U.S. Pat. No. 3,316,247)

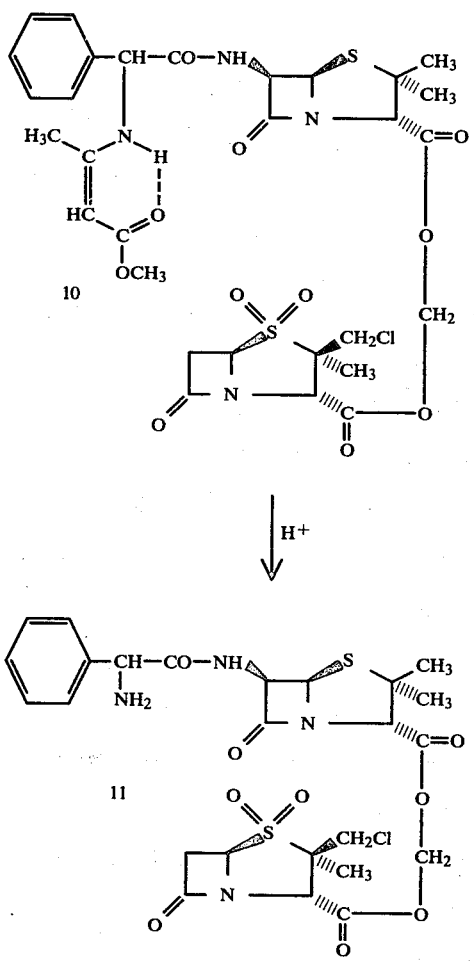

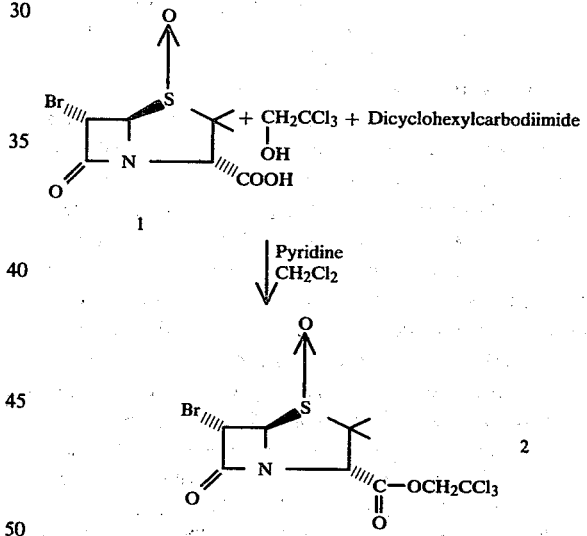

(See page 633 of Cephalosporins and Penicillins, edited by Edwin H. Flynn, Academic Press, New York, 1972)

To a stirred mixture cooled in an ice-bath of 5.46 g. (0.01 mol) of the indicated Dane salt of ampicillin 9 (which was solvated with one molecule of isopropyl alcohol) in 60 ml. acetone there was added 4.08 g. (0.01 ml) of the iodomethyl ester of BL-P2013 (8) and the resulting nearly clear solution was stirred for five hours with the ice-bath removed after 30 minutes. Then most of the acetone was removed in vacuum on the roto-vap and the resulting concentrated solution was dissolved in 200 ml. cold ethyl acetate which was then washed with 2×50 ml. ice cold water and 2×100 ml. saturated aqueous $Na_2SO_4$. The ethyl acetate solution was then dried over $Na_2SO_4$, filtered and most of the ethyl acetate was removed in vacuo on the roto-vap. The residue was triturated with 2×200 ml. dry diethyl ether and the resulting solids were collected by filtration to give 5.5 g. of 10 as a pinkish powder. This powder was stirred in a mixture of 50 ml. water, 50 ml. n-butanol and 20 ml. ethyl acetate while 6 N HCl was added dropwise to pH 2.5. Then occasionally a drop or two of HCl was added to keep the pH at 2.2-2.5 over 45 minutes. When the pH no longer drifted upward there was added to this mixture 100 ml. diethyl ether with good stirring. The aqueous phase was separated and combined with a second 25 ml. $H_2O$ extract of the organic layer. The aqueous solution was extracted once with 50 ml. diethyl ether and the ether was discarded.

The aqueous layer was then stirred vigorously under a layer of 100 ml. 2-butanone (methyl ethyl ketone) while $Na_2SO_4$ was added to saturate the aqueous layer. The 2-butanone layer was separated, dried over $Na_2SO_4$ for 30 minutes in an ice-bath, filtered and concentrated in vacuo to near dryness. The residual oil was triturated to a solid with n-butanol, washed well with ether, then n-pentane, air-dried and then vacuum-dried over $P_2O_5$ at <1 mm Hg pressure to yield 1.6 g. 6-[(R)-2-amino-2-phenylacetamido]-3,3-dimethyl-7-oxo-4-thia-1-azabicyclo[3.2.0]heptane-2-carbonylmethyl 2β-chloromethyl-2-α-methylpenam-3α-carboxylate sulfone (11) in crude form. The IR and nmr spectra were consistent with structure 11 but not with high purity. This solid product was estimated to contain at least 40% and perhaps as much as 80% 6-[(R)-2-amino-2-phenylacetamido]3,3-dimethyl-7-oxo-4-thia-1-azabicyclo[3.2.0]heptane-2-carbonyloxymethyl 2β-chloromethyl-2-α-methylpenam-3α-carboxylate sulfone.

EXAMPLE 22

Improved Synthesis of BL-P2013

This procedure simplifies production of BL-P2013 by eliminating the previous use of catalytic reduction.

Step 1

6α-Bromopenicillanic acid sulfoxide (1) (30 g., 0.1 mol) was dissolved in 1 l. dry $CH_2Cl_2$ followed by the addition of 16.2 ml. (0.2 mol) pyridine and 29.8 g. (0.2 mol) trichloroethanol. Then 20 g. (0.1 mol) of dicyclohexylcarbodiimide was added and the mixture was stirred at 22° for 16 hours. Dicyclohexylurea began to precipitate out; at the end it was removed by filtration. The filtrate was washed with 200 ml. of 5% aqueous sodium bicarbonate, 200 ml. of 10% phosphoric acid and 100 ml. of saturated aqueous sodium sulfate. The organic phase was dried over sodium sulfate at 5° C. for 30 minutes, filtered and evaporated to an oil. Diethyl ether was added and, with scratching, the product 2 crystallized out (27 g., 63% yield).

Step 2

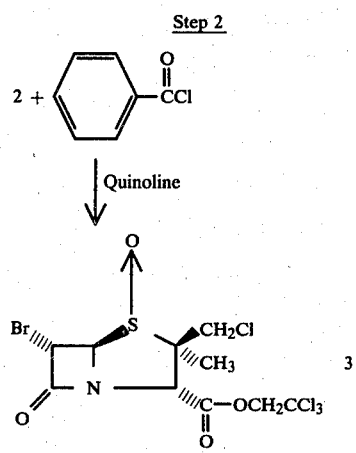

Compound 2 (26.5 g., 0.062 mol) was dissolved in 500 ml. p-dioxane and there was added 8.5 ml. (0.078 mole) benzoyl chloride and 8.75 ml. (0.078 mole) quinoline. The solution was refluxed for four hours and then poured into 1100 ml. water and the product 3 was extracted into 2×400 ml. ethyl acetate. The ethyl acetate extracts were combined, successively washed with 200 ml. 5% aqueous sodium bicarbonate, 200 ml. 5% phosphoric acid and 200 ml. saturated aqueous sodium sulfate, dried over sodium sulfate at 5° C. for thirty minutes and evaporated to an oil (3) which was used "as is" for the next reaction.

Step 3

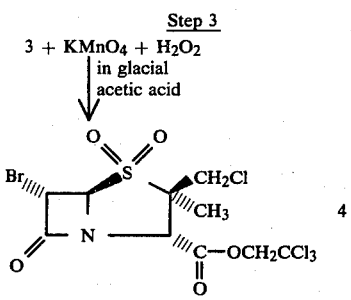

Compound 3 obtained in the previous step was dissolved in 1 l. glacial acetic acid and, with stirring at 22° C., a saturated aqueous solution of KMnO₄ was added dropwise until a pink color persisted (that is, a drop placed on a piece of filter paper gave a pink coloration). Then with cooling 30% H₂O₂ was added dropwise until a clear solution was obtained; some white precipitate was present. The solution was poured into 2.5 l. water and the product 4 was extracted into 3×500 ml. ethyl acetate. The ethyl acetate was washed with 5% aqueous sodium bicarbonate until neutral (that is, no more bubbling upon addition), dried over sodium sulfate and evaporated to leave 4 as the residue. It was left at 10° C. for one day and then triturated with "Skellysolve B" to yield 9.1 g. solid 4. The yield was 28% of theory for steps 2 and 3 combined.

Step 4

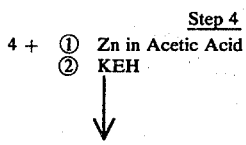

-continued
Step 4

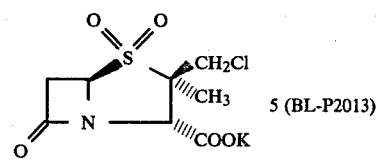

(See U.S. Pat. No. 4,164,497)

Zinc dust (3.75 g.) was slurried in 5 ml. glacial acetic acid and cooled to 5° C. To this mixture there was added a solution of 4 (3 g.; 0.0057 mole) in 15 ml. dimethylformamide and the resulting slurry was stirred at 5° for 2.5 hours.

The zinc was then filtered off and the pale yellow solution was poured into 80 ml. of 5% aqueous hydrochloric acid. That mixture was extracted with 3×25 ml. ethyl acetate. The combined ethyl acetate extracts were extracted with 3×20 ml. of 5% aqueous sodium bicarbonate, saving the ethyl acetate phase after separation.

The bicarbonate extracts were combined, placed under a layer of ethyl acetate, adjusted to pH 1.5 by the addition of 2 N HCl and saturated with sodium sulfate. The ethyl acetate was separated and the aqueous phase was extracted with 2×30 ml. ethyl acetate.

All of the ethyl acetate phases above were combined, dried over sodium sulfate and evaporated to an oil (which was the free acid form of BL-P2013) which was dissolved in about 20 ml. acetone to which 20 ml. diethyl ether was then added. Then 50% potassium 2-ethylhexanoate (KEH) in dry n-butanol was added to neutrality. The product 5 (BL-P2013) crystallized out. After stirring 0.5 hour at 22° it was collected by filtration to yield 650 mgm. of 5 (37% yield).

A 50 mgm. sample of 5 was dissolved in 0.5 ml. water and 20 mgm. N,N'-dibenzylethylenediamine (DBED) diacetate was added. The DBED salt of 5 crystallized out, was collected by filtration, washed with water and dried over P₂O₅ under vacuum to yield N,N'-dibenzylethylenediamine 2β-chloromethyl-2-methylpenam-3-carboxylate sulfone (DBED salt of free acid 5).

Another sample of 5 (450 mgm.) was dissolved in 3 ml. water to which was added a solution of 270 mgm. DBED diacetate in 2 ml. H₂O. With scratching the DBED salt of 5 crystallized out (430 mgm.). Recrystallization from about 5 ml. boiling acetone yielded 270 mgm.

EXAMPLE 23

6-[(R)-2-Amino-2-p-hydroxyphenylacetamido]-3,3-dimethyl-7-oxo-4-thia-1-azabicyclo[3.2.0]heptane-2-carbonyloxymethyl 2β-chloromethyl-2-α-methylpenam-3α-carboxylate sulfone having the formula

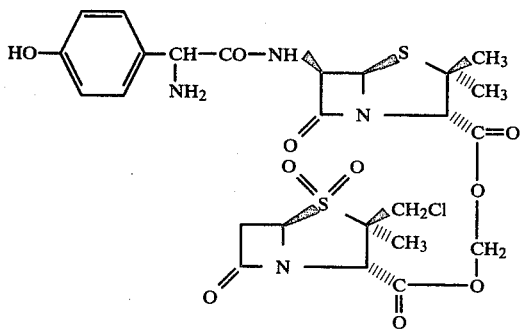

is produced by substituting the corresponding Dane salt of amoxicillin for the ampicillin used in the procedure of Example 21.

EXAMPLE 24

A. Potassium 6-β-[N-(1-Methoxycarbonyl-propen(-2-yl)-D-α-amino-(4-hydroxyphenyl)acetamido]-penicillanate

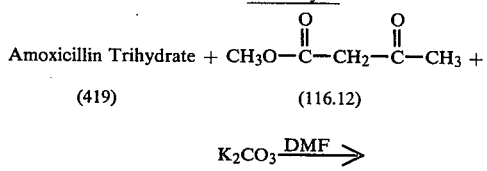

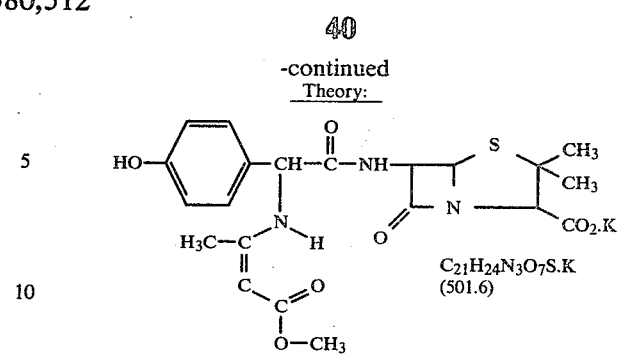

Experimental:

To a stirred suspension of ground (mortar) K₂CO₃ (0.55 mol) in DMF (625 ml) was added 108 ml (01.0 mol) of methylacetoacetate (EKC) followed by 209.5 (0.5 ml) of amoxicillin trihydrate and the mixture was stirred 4 hours at 22° C.±2° C. and then 2 hours at 0°–5° C. (ice bath). The mixture was filtered* and ether (2.5 liters) was added with good stirring and the mixture was left to stand for 30 minutes. The ether was decanted from the oil and 2×2 liter ether portions (triturates) were added and stirred to remove most of the DMF. Then acetone (one liter) was added and with vigorous stirring the product crystallized, was collected by filtration, washed with acetone, dissolved in DMF (600 ml) and the procedure repeated giving an air-dried yield of 144 g of potassium 6-β-[N-(1-methoxycarbonylpropen)-2-yl)-D-α-amino-(4-hydroxyphenyl)acetamido]penicillanate. High-vacuum over P₂O₅ at <1 mm Hg gave 142 g. Dec. pt. 232°–234° C.

*"Dicalite" pad with suction+2×30 ml DMF washes. "Dicalite" is diatomaceous earth.

B. 2-(β-Chloromethyl)-2-methyl-1,1-dioxypenam-3-carbonyloxymethyl-6-[D-(—)-α-amino-α-phenylacetamido]-penicillanate Hydrochloride (BL-P2044)

Theory:

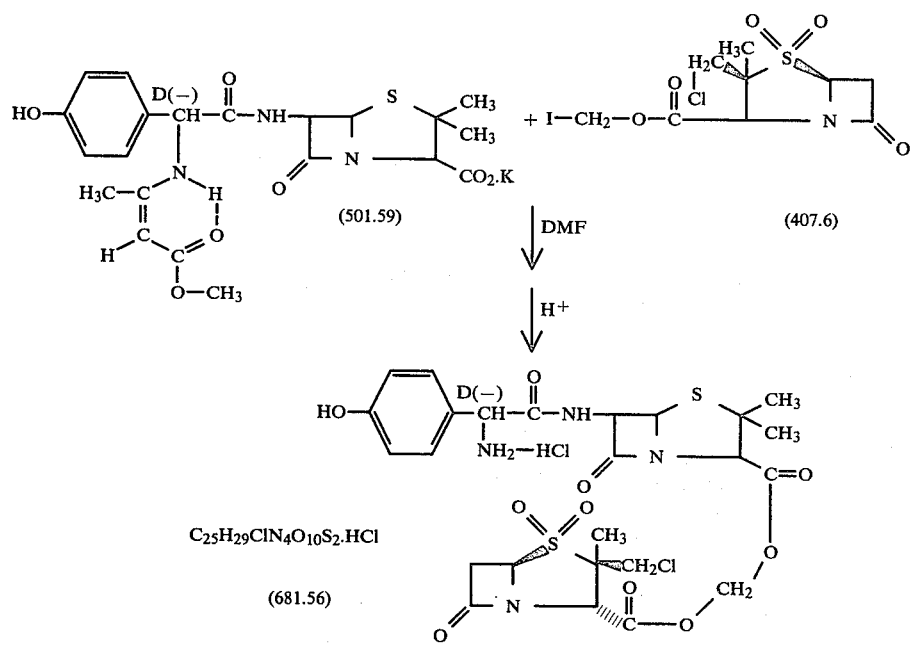

41

Experimental:

To a stirred and cooled solution of 5 g. (0.01 mole) of potassium 6-β-[N-(1-methoxycarbonyl-propen(-2-yl)-D-α-amino-(4-hydroxyphenyl)acetamido]-penicillanate in 17 ml of dry DMF (dried over 3 A molecular sieves), was added 4 g. (0.01 mole) iodomethyl ester of BL-P2013 in portions over a 15 minute period at 3°–8° C. The resulting solution was stirred an additional 15 minutes and then poured onto a vigorously stirred, ice cold mixture of 80 ml of ethyl acetate and 40 ml of saturated CaCl₂ solution. The mixture was filtered rapidly with suction through a "Dicalite" pad. The organic layer was washed twice more with 30 ml portions of saturated CaCl₂ solution. The ethyl acetate solution was then concentrated in vacuo at 22° C. on the flash evaporator to a volume of about 10 ml then 50 ml of n-butanol and 50 ml of H₂O were added plus 50 ml of ethyl acetate and 3 N HCl was added dropwise, with good stirring to maintain the pH at 2.5. The pH was kept at 2.5±0.5 pH units for 30 minutes then ether was slowly added (about 100–150 ml). The aqueous layer was separated and another 25 ml H₂O extract was taken and combined with the first. The H₂O layer was then layered with methyl ethyl ketone (2-butanone) (MEK) 200 ml and salt (NaCl) added until the mixture was saturated. Stirring was continued vigorously for about 15 minutes. The "MEK" layer was separated, dried briefly over Na₂SO₄ at 10° C. (ice bath), filtered, then concentrated in vacuo on the roto-vap to near dryness. The residual oil was triturated and stirred with 30 ml of n-butanol for one hour until a nearly white solid was obtained. The product was collected by filtration, washed with n-butanol then ether (10×20 ml) then n-pentane (10×20 ml) and air dried to yield 800 mg of 2-(β-chloromethyl)-2-methyl-1,1-dioxypenam-3-carbonyloxymethyl-6-[D-(−)-α-amino-α-phenylacetamido]penicillanate hydrochloride. After high-vacuum drying over P₂O₅ at <1 mm Hg for 18 hours there was 760 mg.; and the nmrs run in DMSO and DMSO+D₂O were entirely consistent with the desired structure. Dec. pt. 200°–205° C. (darken above 150° C.).

EXAMPLE 25

2β-Chloromethyl-2α-methyl-1,1-dioxopenam-3-carbonyloxymethyl 6-(D-2,2-dimethyl-5-oxo-4-phenyl-1-imidazolidinyl)-penicillanate Hydrochloride (BL-P2048).

Theory:

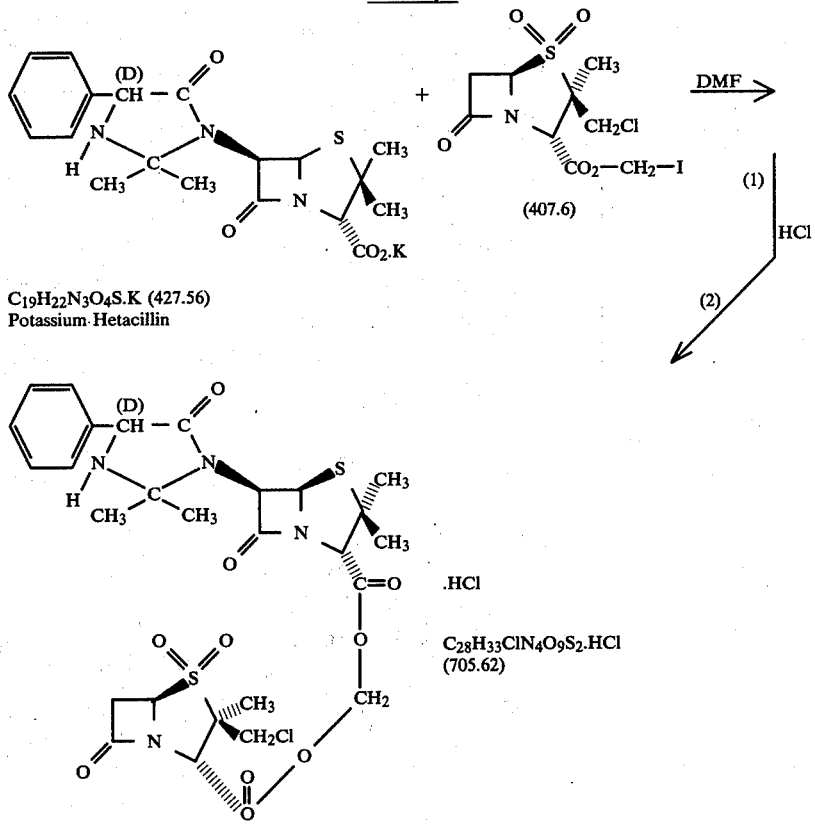

C₁₉H₂₂N₃O₄S.K (427.56)
Potassium Hetacillin

C₂₈H₃₃ClN₄O₉S₂.HCl (705.62)

Experimental:

To a stirred, partial solution of 2.2 g (0.051 mol) of potassium hetacillin in 9 ml of dry DMF (dried over 3 A molecular sieves), cooled to −20° C., was added, in portions, 2.2 g (0.0054 mol) of iodomethyl 2β-chloromethyl-2α-methyl-1,1-dioxopenam-3-carboxylate (iodomethyl ester of BL-P2013) over a 10 minute period. The ice-salt cooling bath was removed and replaced by an ice cooling bath. The solution was stirred at about 3° C. for 15 minutes then the ice bath was removed and the solution was allowed to come to room temperature over a 30 minute period. The dark solution was diluted with 250 ml of ice cold ethyl acetate and washed with 5×30 ml of ice cold water and once with saturated aqueous sodium sulfate solution. The ethyl acetate solution was then stirred in an ice bath with about 1 g of decolorizing carbon ("Darko KB") and anhydrous sodium sulfate for 30 minutes. The mixture was filtered and the carbon and Na₂SO₄ washed with 4×30 ml of ethyl acetate. The combined filtrates were concentrated under reduced pressure at 22° C. to a frothy solid. This was triturated twice with ether (2×25 ml) and then n-pentane (2×25 ml) and finally ether again. The solid off-white powder was collected by filtration, washed with n-pentane, air dried and vacuum dried over P$_2$O$_5$ at <1 mm. Yield, 2.45 g of crude ester.

This material was dissolved in 35 l of ethyl acetate and then, with good stirring, a solution of dry HCl in anhydrous ether was added a few drops at a time until the ethyl acetate mixture was pH 2 to moist pH paper. A small amount of colored solids were filtered off (100–200 mg) and discarded. Ether 200 ml) was added with stirring and the white solids that precipitated were collected by filtration, generously washed with ether and then pentane, air dried then vacuum dried to give 700 mg of product 2β-chloromethyl-2α-methyl-1,1-dioxopenam-3-carbonyloxymethyl 6-(D-2,2-dimethyl-5-oxo-4-phenyl-1-imidazolidinyl)penicillanate hydrochloride. The ir and nmr spectra were consistent with the desired structure. Dec. pt. >140° C. indefinite.

Anal. Calcd for C$_{28}$H$_{33}$ClN$_4$O$_9$S$_2$.HCl: C, 47.49; H, 4.85; N, 7.98; Cl, 10.00. Found: C, 47.25; H, 4.57; N, 8.25; Cl, 9.12; K.F. H$_2$O, 0.90.

IR: 1790 cm$^{-1}$, 1730 cm$^{-1}$. H-NMR(DMSO). δ1.3–1.9(m, 15H,(5,CH$_3$'s)), 3.1–3.8(m,2H,C$_6$-H$_2$(CMPASO$_2$)); 3.8–4.4(m,2H,-CH$_2$Cl) 4.6(s,1H,C$_3$H(Heta)); 4.95(s,1H,C$_3$H (CMPASO$_2$)); 5.25(m,1H,C$_5$-H(CMPASO$_2$)); 5.4–5.6(m,2H, C$_5$H+C$_6$H(Heta)); 5.65(s,1H,φ-CH); 6.0(s,2H,-O-CH$_2$-O);

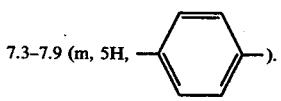

7.3–7.9 (m, 5H, —⌬—).

A second crop of 800 mg was obtained by adding excess ether-HCl solution to the filtrate (which did not include the pentane washes) and immediately filtering off the snow-white ppt. and washing and drying as before. Decomposition point: >150° C. indefinite. The NMR spectrum was better defined. IR: 1790 cm$^{-1}$ (β-lactams and esters overlapping) 1730 cm$^{-1}$ imidazolidine carbonyl. H-NMR(DMSO) (Varian XL-100): δ1.3–1.9 (m,15H,5, CH$_3$'s); 3.1–3.8(m,2H,C$_6$-H$_2$(CMPASO$_2$)); 3.8–4.4(m,2H,-CH$_2$Cl); 4.6 (s,1H,C$_3$H(Heta)); 4.95(s,1H,C$_3$-H(CMPASO$_2$)); 5.25(m,1H, C$_5$-H(CMPASO$_2$)); 5.4–5.6(m,2H,C$_5$H,C$_6$H, Heta), 5.65(s,1H, φ-CH-); 6.0(s,2H,O-CH$_2$-O);

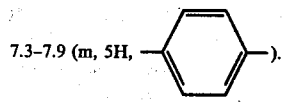

7.3–7.9 (m, 5H, —⌬—).

Anal. Calcd. for C$_{28}$H$_{33}$ClN$_4$O$_9$S$_2$.HCl: C, 47.49; H, 4.85; N, 7.98; Cl, 10.00. Found: C, 47.44; H, 4.80; N, 8.11; Cl, 9.69; K.F. H$_2$O, 1.25.

EXAMPLE 26

A. Potassium Heta-amoxicillin

Theory:

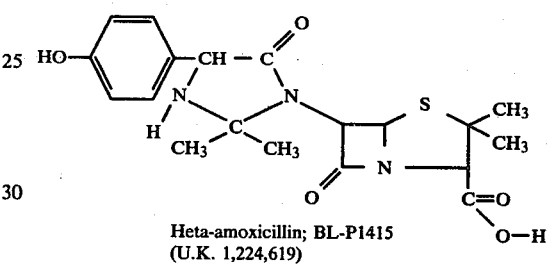

Heta-amoxicillin; BL-P1415
(U.K. 1,224,619)

+ "KEH"
(0.1 mol = 38.5 ml)

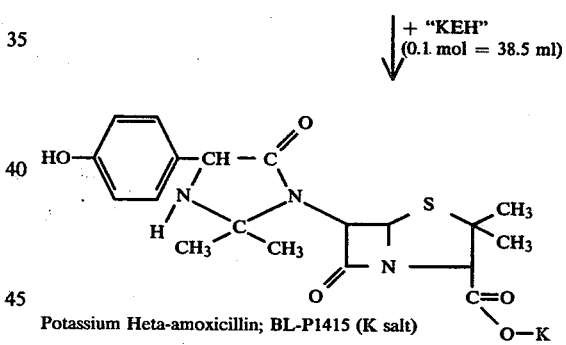

Potassium Heta-amoxicillin; BL-P1415 (K salt)

Experimental:

To a stirred suspension of 40.4 g (0.1 mole) of BL-P1415 in 400 ml of acetone was added 38.5 ml (0.1 ml) of "KEH" (potassium 2-ethylhexanoate in n-butanol) and the mixture was stirred and scratched. 400 ml more acetone was then added and the slurry stirred for 2 hours. The product was collected by filtration, washed with 4×100 ml. acetone, 4×200 ml. ethyl acetate, 4×200 ml ether then 4×100 ml of n-pentane and air dried overnight to give 42 g. High-vacuum drying at <1 mm Hg for 6 hours gave 40.5 g of potassium heta-amoxicillin. (92% yield). Dec. pt. 208°–210° C.

B.
2β-Chloromethyl-2α-methyl-1,1-dioxopenam-3-carbonyloxymethyl 6-[D-2,2-dimethyl-5-oxo-4-(4-hydroxyphenyl)-1-imidazolidinyl]-penicillanate Hydrochloride (BL-P2049)

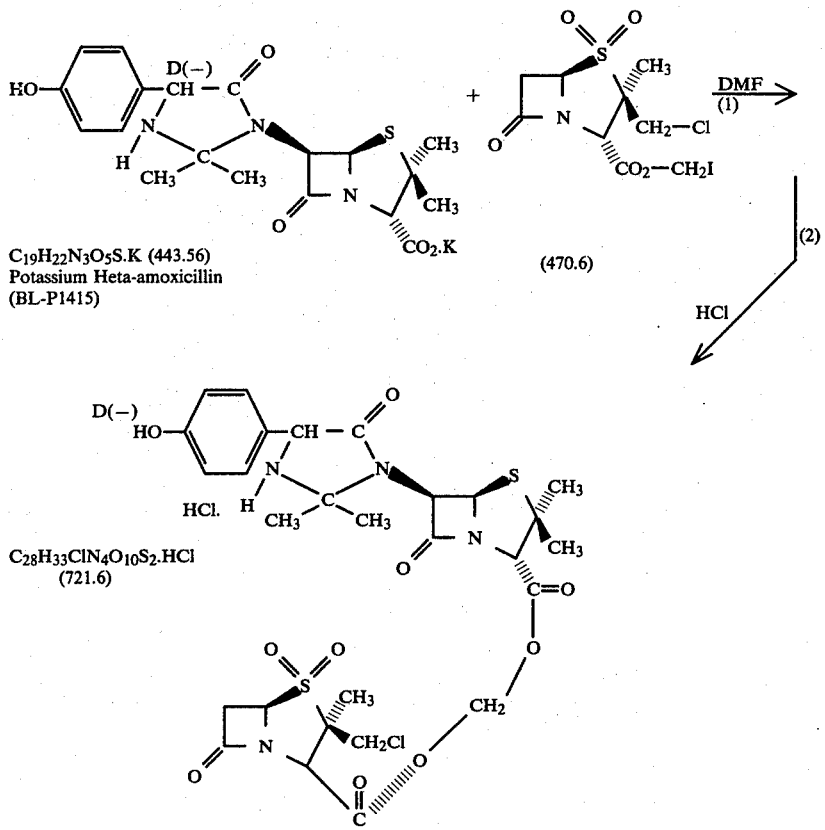

To a stirred solution of 4.4 g (0.01 mol) of BL-P1415 (K-salt) in 10 ml of dry DMF at 3° C. (ice bath) was added in portions 4 g (0.01 mol) of the iodomethyl ester of BL-P2013 over a 10 minute period. Stirring was continued for 20 minutes at 3° C. The resulting solution was diluted with 100 ml of ice cold ethyl acetate and 20 ml of ice cold water. The H$_2$O layer was separated and the organic layer washed 4 more times with ice water (25 ml) then once with aqueous saturated Na$_2$SO$_4$ solution (40 ml). The organic layer was separated and filtered through anhydrous Na$_2$SO$_4$ and the Na$_2$SO$_4$ washed 3×25 ml of ethyl acetate. The combined filtrates were concentrated under reduced pressure to a froth at 22° C. The froth was re-dissolved in 100 ml of ethyl acetate and filtered. It was then stirred rapidly while dry HCl dissolved in dry ether was added dropwise until no more precipitate formed. The precipitate was immediately collected by filtration, washed with dry ether then pentane (5×25 ml) and air dried. Yield 3 g. After vacuum drying over P$_2$O$_5$ for 5 hours there was obtained 2.9 g of product 2β-chloromethyl-2α-methyl-1,1-dioxopenam-3-carbonyl-oxymethyl 6-[D-2,2-dimethyl-5-oxo-4-(4-hydroxyphenyl)-1-imidazolidinyl]-penicillanate hydrochloride. Dec. pt. 188°–195° with slow dec. above 140° C. The ir and nmr spectra were consistent with the desired structure.

Anal. Calcd. for C$_{28}$H$_{33}$ClN$_4$O$_{10}$S$_2$.HCl: C, 46.58; H, 4.75; N. 7.76; Cl. 9.82. Found: C, 47.34; H, 5.08; N, 7.77; Cl, 9.26; K.F. H$_2$O, 1.07.

IR: 1800 cm$^{-1}$, 1750 cm$^{-1}$ (shoulder), 1140 cm$^{-1}$, 1330 cm$^{-1}$ SO$_2$. H-NMR(DMSO) (Varian XL-100) δ6.7–7.5

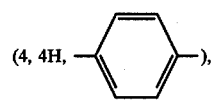 (4, 4H, —⟨⟩—), 5.95 (s,2H,—O—CH$_2$—O—), 5.6(s,1H,φ—C<u>H</u>—), 5.4–5.6 (m,2H,C$_5$<u>H</u>,C$_6$<u>H</u> (Hetamox)), 5.1–5.3 (m,1H,C$_5$—<u>H</u> (CMPASO$_2$)), 5.95 (s,1H,C$_3$<u>H</u> (CMPASO$_2$)), 4.6 (s,1H,C$_3$<u>H</u> (Hetamox)), 3.8–4.5 (m,2H,—C<u>H</u>$_2$Cl), 3.1–3.9 (m,2H,C$_6$—<u>H</u>$_2$ (CMPASO$_2$)), 1.1–1.9 (m,15H,5 CH$_3$'s).

EXAMPLE 27

The following is an alternate synthesis of BL-P2013 which eliminates the need for a catalytic hydrogenation. The synthesis is carried out using the trichloroethyl ester which is removed at the last step along with the 6-bromo group by a zinc-acetic acid reduction.

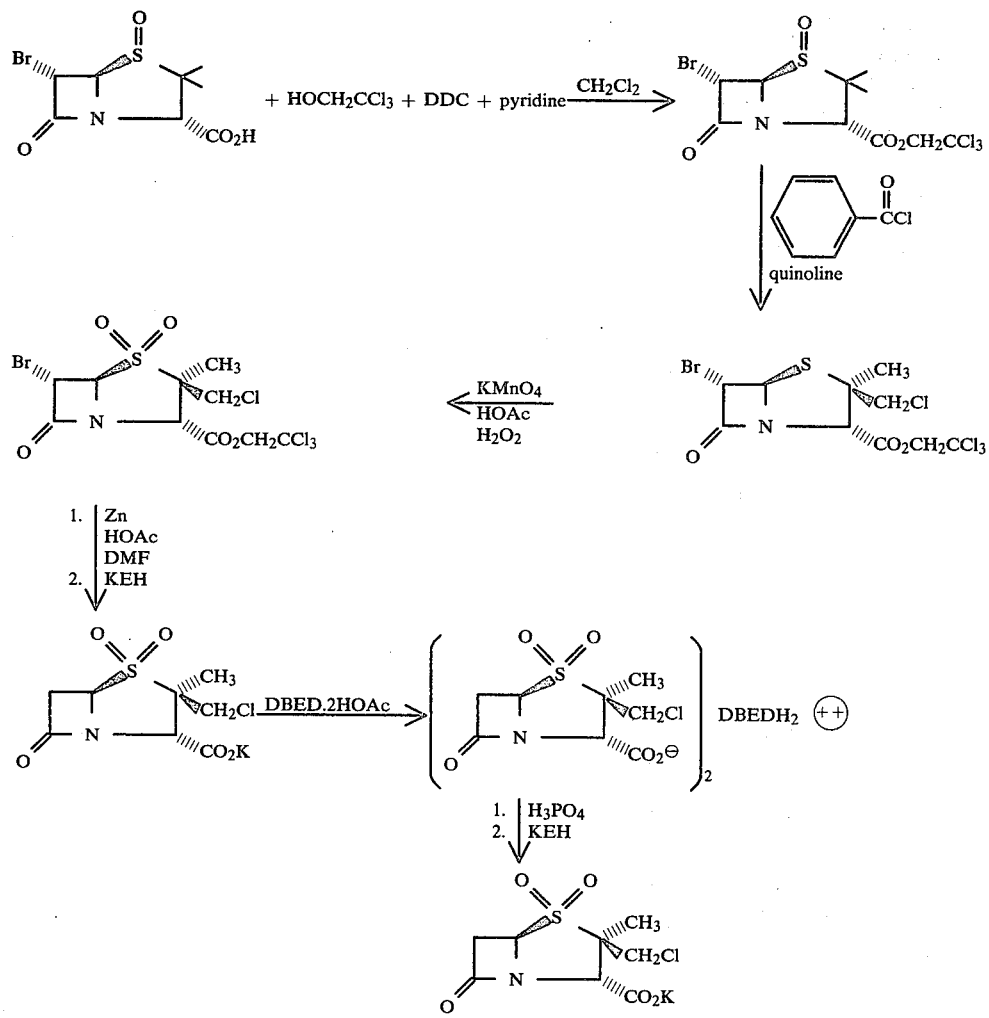

2',2',2'-Trichloroethyl 6α-bromopenicillanate Sulfoxide

To 1 of dry methylene chloride (dried over Linde 4A molecular sieves) was added 30 g (0.1 mole) of 6α-bromopenicillanic acid sulfoxide followed by 16.2 ml (0.2 mole) pyridine and 29.8 g (0.2 mole) of trichloroethanol. Then 20 g. (0.1 mole) of dicyclohexylcarbodiimide (DCC) was added and the mixture stirred at 22° for 16 hours. The precipitate was filtered off and the filtrate was washed with 200 ml of 5% aqueous sodium bicarbonate, 200 ml of 10% aqueous phosphoric acid and 100 ml of saturated aqueous sodium sulfate. The methylene chloride solution was dried over anhydrous sodium sulfate at 5° for ½ hour, filtered and evaporated to an oil. Ethyl ether was added and with scratching, the product crystallized out. It was collected by filtration, washed with ethyl ether, and dried to yield 27 g of 2',2',2'-trichloroethyl 6α-bromopenicillanate sulfoxide (63% yield), mp 125°–126°. The nmr spectrum was consistent for the desired structure.

Anal. Calcd. for $C_{10}H_{11}BrCl_3NO_4S$: C, 28.09; H, 2.59; N, 3.28. Found: C, 29.40; H, 2.97; N, 3.59; K.F. ($H_2O$), 0.40.[1]

2',2',2'-Trichloroethyl 6α-bromo-2β-chloromethyl-2α-methylpenam-3-carboxylate To 500 ml of 1,4-dioxane was added 26.5 g (0.062 mole) of 2',2',2'-trichloroethyl 6α-bromopenicillanate sulfoxide followed by 8.5 ml (0.078 mole) of benzoyl chloride and 8.75 ml (0.078 mole) of quinoline. The solution was refluxed for 4 hours. It was then poured into 1100 ml $H_2O$ and extracted with 2×400 ml ethyl acetate. The ethyl acetate extracts were combined, washed with 200 ml 5% aqueous sodium bicarbonate, 200 ml 5% aqueous phosphoric acid and 200 ml of saturated aqueous sodium sulfate. The ethyl acetate extracts were dried over anhydrous sodium sulfate at 5° for ½ hour, filtered, and the filtrate evaporated to give 2',2',2'-trichloroethyl 6α-bromo-2β-chloromethyl-2α-methylpenam-3-carboxylate as an oil. This material was used for the next reaction without further purification.[2]

2',2',2'-Trichloroethyl 6α-bromo-2β-chloromethyl-2α-methylpenam-3-carboxylate Sulfone The oil from the previous reaction was dissolved in 1 l of glacial acetic acid and, with stirring at 22°, a saturated aqueous solution of potassium permanganate was added dropwise until a pink color persisted for 5 minutes. (A drop placed on a piece of filter paper giving a pink coloration). Then a 30% hydrogen peroxide solution was added dropwise until a clear solution was obtained (some white precipitate was present). The solution was poured into 2½ liters of H₂O and the product extracted into 3×500 ml of ethyl acetate. The combined ethyl acetate extracts were washed with 5% aqueous sodium bicarbonate solution until neutral. It was dried over sodium sulfate at 5° for ½ hour and evaporated to a residue. It was triturated with heptanes ("Skellysolve B") to yield 9.1 g of solid 2',2',2'-trichloroethyl 6α-bromo-2β-chloromethyl-2α-methylpenam-3-carboxylate sulfone. (28% yield for two steps). The nmr spectrum was consistent for structure.[3]

BL-P2013

A slurry of 3.75 g of zinc dust in 5 ml of glacial acetic acid was cooled to 5° and to it was added a solution of 3 g (0.0057 mole) of 2',2',2'-trichloroethyl 6α-bromo-2β-chloromethyl-2α-methylpenam-3-carboxylate sulfone in 15 ml of dimethylformamide. The slurry was stirred at 5° for 2½ hours and the zinc was removed by filtration. The pale yellow filtrate was poured into 80 ml of 5% aqueous hydrochloric acid and extracted with 3×25 ml of ethyl acetate. The combined ethyl acetate extracts were extracted with 3×20 ml of 5% aqueous bicarbonate. (The ethyl acetate contained 600 mg of starting material). The bicarbonate extracts were combined and, under a layer of 30 ml of ethyl acetate, the pH was adjusted to 1.5 by the addition of 2 N HCl. The solution was saturated with sodium sulfate and the ethyl acetate separated. The aqueous layer was extracted with 2×30 ml of ethyl acetate. The combined ethyl acetate extracts were dried over sodium sulfate at 5° for ½ hour and evaporated to an oil. The oil was dissolved in 20 ml of acetone and 20 ml of ether added. Then, 50% potassium 2-ethylhexanoate (KEH) in n-butanol was added dropwise until the pH of the solution was neutral and the product crystallized out. It was collected by filtration to yield 650 mg. (47% yield) of BL-P2013. The nmr spectrum was consistent for structure.[4]

DBED Salt of BL-P2013

A solution of 270 mg (0.00075 mole) at N,N'-dibenzylethylenediamine (DBED) diacetate in 2 ml H₂O was added to 450 mg (0.0015 mole) of BL-P2013 in 3 ml H₂O. With scratching, the DBED salt crystallized out and was filtered off to yield 430 mg. It was recrystallized by dissolving it in 5 ml of boiling acetone and after filtering, the product crystallized out of the cold filtrate. It was left at 5° for ½ hour, collected by filtration and washed with 5 ml of ethyl ether to yield 270 mg (47% yield) of DBED salt of BL-P2013.

Anal. Calcd. for C₁₆H₁₉ClN₂O₅S: C, 49.68; H, 4.95; N, 7.24; Cl, 9.16. Found: C, 49.63; H, 5.50; N, 6.99; Cl, 8.37; K.F. (H₂O), 1.32.

The nmr spectrum was consistent for structure.

BL-P2013.K Salt from the DBED Salt

In a mixture of 2 ml of H₂O and 6 ml of ethyl acetate, 190 mg (0.005 mole) of BL-P2103 DBED salt was suspended and 40% aqueous phosphoric acid was added until the pH was 2. The aqueous layer was separated and reextracted with 3 ml of ethyl acetate. The combined ethyl acetate extracts were dried over sodium sulfate at 5° for ½ hour and filtered. The filtrate was evaporated to a residue and redissolved in 2 ml of acetone and 2 ml of ether. Then 50% potassium 2-ethylhexanoate in n-butanol was added dropwise until the pH was neutral. The potassium salt of BL-P2013 crystallized out, was collected by filtration and dried to yield 90 mg (60% yield). The nmr spectrum was consistent for structure.

Anal. Calcd. for C₈H₉ClKNO₅S.½H₂O: C, 30.52; H, 3.20; N, 4.45; Cl, 11.26; KF, 2.86. Found: C, 30.51; H, 3.50; N, 4.38; Cl, 9.98; KF, 3.35.

The CP-45899 content of this material is estimated to be approximately 5%.

Footnotes

1. This type of reaction can be run using 2,2,2-trichloroethyl chloroformate. The dicyclohexylcarbodiimide method was used because it was more convenient on a lab scale. It may also be advantageous to recrystallize the product.
2. It would be better to crystallize the intermediate at this stage to eliminate any unrearranged material which would lead to CP-45899 at the end of the sequence.
3. In this reaction, the end point was missed and too much potassium permanganate was used. A higher yield would most likely be attained in future runs.
4. The reduction was not complete as seen by the recovery of 20% of the starting material. It should be run at a higher temperature, e.g., 22° and/or for a longer time.

BIOLOGICAL DATA

The product of Example 1, Compound 5, having the structure

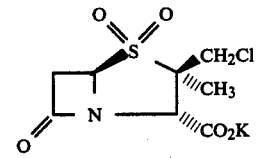

will be referred to below as BL-P2013.

Although at best a very weak antibacterial agent itself, BL-P2013 inhibits β-lactamases and protected ceforanide and amoxicillin from destruction by β-lactamase-producing bacteria in vitro and in vivo when used in combination with those two agents.

TABLE I

| Antibacterial Activity of the New Sulfone | | | |
|---|---|---|---|
| | | MIC (mcg/ml) | |
| Organism | | BL-P2013 | Ampicillin |
| S. pneumoniae | A-9585 | 16 | 0.004 |
| S. pyogenes | A-9604 | 63 | 0.004 |
| S. aureus | A-9537 | >125 | 0.16 |
| S. aureus + 50% serum | A-9537 | >125 | 0.06 |
| S. aureus Pen-Res | A-9606 | >125 | >125 |
| S. aureus Meth-Res | A15097 | >125 | 125 |
| S. faecalis | A20688 | >125 | 0.13 |
| E. coli | A15119 | >125 | 1 |
| E. coli | A20341-1 | >125 | >125 |
| K. pneumoniae | A15130 | >125 | 125 |
| K. pneumoniae | A20468 | >125 | >125 |
| P. mirabilis | A-9900 | >125 | 0.13 |
| P. vulgaris | A21559 | >125 | 125 |
| P. morganii | A15153 | >125 | >125 |
| P. rettgeri | A21203 | >125 | 4 |
| S. marcescens | A20019 | >125 | 16 |
| E. cloacae | A-9659 | >125 | 63 |
| E. cloacae | A-9656 | >125 | >125 |

TABLE I-continued

Antibacterial Activity of the New Sulfone

| Organism | | MIC (mcg/ml) | |
| --- | --- | --- | --- |
| | | BL-P2013 | Ampicillin |
| P. aeruginosa | A-9843A | >125 | >125 |
| P. aeruginosa | A21213 | >125 | >125 |

TABLE 2

Anti-Bacteroides Activity of Ceforanide and Amoxicillin Alone and in Combination with BL-P2013

| Organism | Beta-lacta-mase | Cefo-ranide | Ceforanide +BL-P2013 (1:1) | BL-P 2013 | Amoxicillin +BL-P2013 (1:1) | Amoxi-cillin |
| --- | --- | --- | --- | --- | --- | --- |
| *B. fragilis* | | | | | | |
| A21916 | + | 63 | 2 | >125 | 2 | 8 |
| A22053 | + | 32 | 4 | 63 | 2 | 8 |
| A22021 | + | 32 | 2 | 32 | 2 | 4 |
| A21875 | + | 32 | 4 | 63 | 2 | 8 |
| A22534 | + | >125 | 32 | 125 | 16 | >125 |
| A22697 | + | 63 | 8 | 63 | 2 | 8 |
| A22693 | + | 63 | 4 | 63 | 2 | 16 |
| A22694 | + | 125 | 16 | 63 | 2 | 16 |
| A22695 | + | >125 | 16 | 32 | 4 | 125 |
| A22696 | + | >125 | 32 | 63 | 8 | >125 |
| A22533 | + | >125 | 32 | 32 | 32 | >125 |
| A22535 | + | >125 | 32 | 125 | 32 | >125 |
| A22792 | + | >125 | 8 | 32 | 4 | 125 |
| A22793 | + | 32 | 4 | 32 | 2 | 8 |
| A22794 | + | 32 | 4 | 32 | 2 | 8 |
| A22795 | + | 63 | 4 | 32 | 4 | 16 |
| A22797 | + | 63 | 4 | 63 | 2 | 16 |
| A22798 | + | 32 | 4 | 63 | 2 | 8 |
| *B. theta-iotaomi-cron* | | | | | | |
| A22277 | + | 125 | 4 | 63 | 2 | 16 |
| A22279 | + | 125 | 8 | 63 | 4 | 16 |
| *Bacteroides species* | | | | | | |
| A20934 | + | 32 | 4 | 32 | 2 | 8 |
| A21959 | + | 63 | 4 | 32 | 2 | 16 |
| A20929 | + | 63 | 4 | 32 | 2 | 16 |
| A21954 | + | 63 | 16 | 63 | 2 | 16 |
| A20933 | + | 63 | 16 | 63 | 4 | 8 |
| A20930 | + | 125 | 8 | 125 | 4 | 32 |
| A20931 | + | 63 | 4 | 32 | 2 | 16 |
| A20927-1 | − | 0.5 | 1 | 63 | 0.13 | 0.13 |
| A20935 | − | 2 | 2 | 125 | 0.13 | 0.13 |

— good synergism
- - - marginal synergism

*Minimum inhibitory concentration (MIC) determined by the agar dilution method using 50X dilutions of 24 hour cultures as inocula dispensed by the Steer's inoculator. Assay medium composed of Brucella Agar plus 5% laked sheep blood and 10 mcg/ml vitamin K.

TABLE 3

**Therapeutic Efficacy of Amoxicillin in Combination with BL-P2013 in Mice Experimentally Infected with a Beta-Lactamase Strain of *Staphylococcus aureus***

| Chal-lenge (No. of Organ-isms) | PD₅₀/Treatment (mg/kg) | | | | | |
| --- | --- | --- | --- | --- | --- | --- |
| | Amoxicillin (A) | | BL-P2013 (B) | | A + B (1:1) | |
| | IM | PO | IM | PO | IM | PO |
| *S. aureus* A-9606 5 × 10⁸ | >800 | >800 | >50 | >200 | 6.3 | 44 |
| 5 × 10⁸ | >800 | >800 | >50 | >200 | 19 | 77 |
| 7 × 10⁸ | >800 | — | >50 | — | 9.6 | — |

Treatment schedule: Drugs were administered 0 and 2 hours post-infection.

TABLE 4

Blood levels of BL-P2013 and its Pivaloyloxymethyl Ester (BL-P2024) After Oral Administration to Mice

| Compound | Dose (mg/kg) | Blood Level (µg/ml) | | | | | | Half-life (min.) | Assay Organism |
| --- | --- | --- | --- | --- | --- | --- | --- | --- | --- |
| | | 15 | 30 | 60 | 90 | 120 | 150 | | |
| | | Minutes After Administration | | | | | | | |
| BL-P2013 | 100 | 4.5 | 5.1 | 3.9 | 2.3 | 1.5 | 0.8 | 50 | *E. coli* A-9675 |
| | 100 | 4.6 | 4.1 | 3 | <2.6 | <2.6 | <2.6 | — | *S. aureus* A-9606 |
| | 200 | 7.4 | 9.8 | 7.1 | 4.1 | 2.8 | <2.6 | 50 | *S. aureus* A-9606 |
| BL-P2024 | 100 | 12.8 | 12.9 | 9.7 | 7.2 | 5.5 | 4.2 | 70 | *E. coli* A-9675 |

TABLE 4-continued

Blood levels of BL-P2013 and its Pivaloyloxymethyl Ester (BL-P2024) After Oral Administration to Mice

| Compound | Dose (mg/kg) | Blood Level (μg/ml) 15 | 30 | 60 | 90 | 120 | 150 | Half-life (min.) | Assay Organism |
|---|---|---|---|---|---|---|---|---|---|
| | | Minutes After Administration | | | | | | | |
| | 100 | 13.1 | 12 | 8 | 5.7 | 3.8 | <2.5 | 60 | S. aureus A-9606 |
| | 200 | 14.7 | 14.4 | 9.8 | 8.7 | 5.1 | <2.5 | 60 | S. aureus A-9606 |

Values represent averages of two to four test.

TABLE 5

Blood Levels and Half-Life of BL-P2024 After Oral Administration of Various Doses to Mice

| Compound | Dose (mg/kg) | Blood Level (μg/ml) 15 | 30 | 60 | 90 | 120 | 150 | t½ (min.) |
|---|---|---|---|---|---|---|---|---|
| | | Minutes After Administration | | | | | | |
| BL-P2024 | 25 | 5.9 | 6.2 | 3.6 | 1.9 | 1.3 | 0.7 | 40 |
| | 50 | 7.7 | 9.5 | 6.3 | 4.7 | 3.5 | 2.3 | 60 |
| | 100 | 12.3 | 12.2 | 9.4 | 7.2 | 5.7 | 4.6 | 85 |
| | 200 | 14.7 | 14.4 | 9.8 | 8.7 | 5.1 | <2.5 | 60 |

BL-P2024 was suspended in Tween-CMC-water.
Values are averages of 2 experiments for 25 and 50 mg/kg doses, 5 to 6 experiments for the 100 mg/kg dose, and 2 to 3 experiments for the 200 mg/kg dose.
Assay organism: E. coli A9675 for all doses except for 200 mg/kg of BL-P2024 (S. aureus A9606).

TABLE 6

Therapeutic Efficacy of Amoxicillin in Combination with BL-P2013 in Mice Experimentally Infected with β-Lactamase Producing Strains of S. aureus and E. coli

| Organism | Challenge (No. of Organisms) | Amoxicillin | Amoxicillin: BL-P2013 4:1 | 2:1 | 1:1 | 1:2 | 1:4 | BL-P 2013 |
|---|---|---|---|---|---|---|---|---|
| S. aureus A9606 | 7 × 10⁸ | >200 | >200:>50 | 44:22 | 33:33 | 38:76 | 25:100 | >200 |
| | 2 × 10⁹ | >800 | | 33:17 | 14:14 | 10:20 | | >200 |
| S. aureus A15091 | 4 × 10⁸ | >200 | 132:66 | 78:39 | 44:44 | | | >200 |
| | 5 × 10⁸ | >800 | | 114:57 | 100:100 | 66:132 | | >200 |
| S. aureus A20379 | 6 × 10⁸ | >200 | 174:44 | 44:22 | 25:25 | 22:44 | 19:76 | 174 |
| | 5 × 10⁸ | >200 | | 50:25 | 43:43 | 35:70 | | >200 |
| E. coli A20649 | 5 × 10⁵ | >200 | 25:6.3 | 11:5.5 | 11:11 | | | >200 |
| | 6 × 10⁵ | >200 | 20:5 | 8:4 | 6:6 | 10:20 | 63:25 | >200 |
| E. coli A21223 | 7 × 10⁵ | >200 | 6:1.5 | 6:3 | 5:5 | | | >200 |
| | 6 × 10⁵ | >200 | 8:2 | 6:3 | 6:6 | 4:8 | 3.5:14 | >200 |
| | 7 × 10⁵ | >200 | | 7:3.5 | | | | >200 |
| E. coli A9675 | 8 × 10⁵ | >200 | 8:2 | 6:3 | 3:3 | 4:8 | 4:16 | >200 |
| | 7 × 10⁵ | >100 | 10:2.5 | 6:3 | 7:7 | 2.5:5 | | >100 |
| | 6 × 10⁵ | >400 | 13:3.3 | 6:3 | 5:5 | 5:10 | | >200 |

Treatment schedule: Drugs were administered orally at 0 and 2 hours post-infection.
Drugs were suspended in TCMC.

TABLE 7

Therapeutic Efficacy of Amoxicillin in Various Combinations with the Pivaloyloxymethyl Ester (BL-P2024) of BL-P2013 in Mice Experimentally Infected with β-Lactamase Producing Strains of S. aureus and E. coli

| Organism | Challenge (No. of Organisms) | Drug-Vehicle[b] | Amoxicillin | Amoxicillin: BL-P2024 4:1 | 2:1 | 1:1 | BL-P 2024 |
|---|---|---|---|---|---|---|---|
| S. aureus A15091 | 5 × 10⁸ | TCMC | >800 | | 66:33 | 57:57 | >200 |
| S. aureus A20379 | 5 × 10⁸ | TCMC | >800 | | 12:6 | 9:9 | 200 |
| E. coli A9675 | 9 × 10⁵ | 50% DMSO | >100 | 12:12 | 6:3 | 3:3 | >25 |
| E. coli A9675 | 7 × 10⁵ | 50% DMSO | >100 | 10:2.5 | 7:3.5 | 4:4 | >25 |
| E. coli A9675 | 7 × 10⁵ | TCMC | >100 | 8:2 | 6:3 | 5:5 | >25 |
| E. coli A9675 | 6 × 10⁵ | TCMC | >400 | 9.2:2.4 | 7:3.5 | 7:7 | >200 |

PD$_{50}$/Treatment (mg/kg)[a]

[a]Mice treated orally at 0 and 2 hours post-infection.
[b]Amoxicillin: BL-P2024 combinations were soluble in 50% DMSO. Amoxicillin was soluble in TCMC (aqueous Tween-carboxymethylcellulose) whereas BL-P2024 was administered as a suspension in that vehicle.

TABLE 8

Oral Mouse Blood Levels of BL-P2036 and BL-P2013 or BL-P2024

| Compound | Dose (mg/kg) | 15 | 30 | 60 | 90 | 120 | 150 |
|---|---|---|---|---|---|---|---|
| | | \multicolumn{6}{c}{Blood Levels (mcg/ml) Minutes After Administration} | | | | | |
| \multicolumn{8}{c}{Test Number 1} | | | | | | | |
| BL-P2036 | 25 | 1.7 (1.3–2.3) | 2.3 (2–2.6) | 0.9 (0.6–1.3) | <0.6 | <0.6 | <0.6 |
| BL-P2036 | 50 | 2.8 (1.6–4.8) | 3.3 (2–5.3) | 2.5 (1.2–5.3) | 1.3 (0.7–2.4) | 0.8 (0.5–1.5) | <0.6 |
| BL-P2036 | 100 | 3.6 (2.6–4.9) | 3.9 (2.9–5.1) | 3.2 (2.4–4.4) | 2 (1.5–2.7) | 1.5 (1.1–2.1) | 0.8 (0.7–1.0) |
| BL-P2013 | 25 | 1.3 (1.1–1.6) | 1.4 (1.2–1.6) | 1.0 (0.8–1.2) | <0.6 | <0.6 | <0.6 |
| BL-P2013 | 50 | 2.2 (1.8–2.7) | 2.6 (2.1–3.2) | 1.9 (1.4–2.6) | 1.5 (1.1–2.1) | 1.1 (0.8–1.4) | 0.8 (0.5–1.3) |
| BL-P2013 | 100 | 3.4 (2.1–5.4) | 4.5 (3.6–5.7) | 3.9 (3.4–4.6) | 3.6 (2.5–5) | 2.7 (1.7–4.3) | 2.1 (1.4–3.2) |
| \multicolumn{8}{c}{Test Number 2} | | | | | | | |
| BL-P2024 | 25 | 3.7 (2.6–5.5) | 4.3 (3–6.2) | 2.3 (0.9–5.8) | 0.8 (0.4–1.8) | <0.6 | >0.6 |
| BL-P2024 | 50 | 5 (0.8–33.3) | 4.5 (1.5–13.4) | 4.9 (2.4–9.8) | 3.6 (3.1–4.1) | 2.6 (1.5–4.3) | 1.7 (0.9–3.1) |
| BL-P2024 | 100 | 8.3 (5.5–12.6) | 9.5 (5.2–17.5) | 7.8 (4.2–14.3) | 4.8 (3.4–6.7) | 3.9 (2.2–6.8) | 3.7 (2.8–5) |
| BL-P2036 | 25 | 3.6 (2.2–5.9) | 3.3 (2.2–4.7) | 2.1 (1.6–2.8) | 1.4 (0.7–2.8) | 0.8 (0.4–1.7) | <0.6 |
| BL-P2036 | 50 | 4.0 (3–5.3) | 3.6 (1.4–9) | 2.2 (1.4–3.7) | 2.1 (1.3–3.6) | 1.5 (0.6–3.6) | 1.0 (0.5–2.4) |
| BL-P2036 | 100 | 4.9 (3.7–6.5) | 6.5 (3.7–11.5) | 4.5 (3.4–5.9) | 2.8 (2.2–3.6) | 1.9 (1–3.7) | 1.3 (0.4–4) |
| \multicolumn{8}{c}{Test Number 3} | | | | | | | |
| BL-P2013 | 25 | 1.4 (1.1–1.9) | 2.0 (1.5–2.6) | 1.4 (0.9–2.1) | 1.2 (0.6–2.3) | <1.2 | <1.2 |
| BL-P2013 | 50 | 4.6 (3–6.9) | 5.5 (3–10.1) | 3.6 (2–6.4) | 3.1 (1.7–5.7) | 2 (0.8–5) | 1.1 (0.8–1.5) |
| BL-P2013 | 100 | 6.8 (4.8–9.6) | 11.5 (7.3–18) | 6.4 (3.2–12.8) | 4.2 (2.1–8.6) | 3.3 (1.4–7.6) | 2.5 (0.7–8.9) |
| BL-P2036 | 25 | 4.3 (2.9–6.5) | 4.5 (2.2–9.2) | 3.5 (1.7–7.2) | 2.5 (1.3–4.8) | 2.2 (1–4.9) | 2.0 (1–3.7) |
| BL-P2036 | 50 | 4.6 (2.3–9.2) | 4.8 (3.3–7.1) | 3.5 (1.8–7) | 2.2 (1.2–4) | 1.9 (1.2–3) | 1.8 (0.3–4.6) |
| BL-P2036 | 100 | 7.1 (3.1–16.2) | 6.7 (3.6–12.3) | 5.8 (3.9–8.5) | 4.3 (3–6) | 4 (2.8–5.6) | 2.7 (1.8–4) |

Compounds prepared in 5% Propylene Glycol & Tween-CMC-H₂O.
Values in parentheses are 95% confidence limits.
Assay Organism: *E. coli* A9675 (pH = 6.6, 0.1% inoculum)

TABLE 9

Mouse Blood Levels of Selected Beta-Lactams After Oral Administration with BL-P2013 as Mutual Pro-Drugs or Mixtures
Test Number 1

| Compound | Dose (mg/kg) | 15 | 30 | 60 | 90 | 120 | 150 | AUC (µg · h/ml) |
|---|---|---|---|---|---|---|---|---|
| | | \multicolumn{6}{c}{Blood Level (µg/ml) Minutes After Administration} | | | | | | |
| BL-P2043 | 50 | 5.1 | 5 | 3 | 1.8 | 1.3 | 1.1 | 6.5 |
| Ampicillin + BL-P2013 | 38 | 5.3 | 4.3 | 2 | 1.1 | 0.8 | 0.6 | 5 |
| | 50 | 1.8 | 3.2 | 3.8 | 3 | 2.4 | 2 | 6.8 |
| | 38 | 1.1 | 1.7 | 2.2 | 1.6 | 1.3 | 1.1 | 3.8 |
| BL-P2048 | 50 | 8* | 8.2 | 6.3 | 3.7 | 2.6 | 1.9 | 11.9 |
| | 38 | 10 | 9.3 | 4 | 1.3 | 0.9 | 0.6 | 9.2 |
| Hetacillin + BL-P2013 | 50 | 1.2* | 2.1 | 3.1 | 3.3 | 3.1 | 2.1 | 6.3 |
| | 38 | 1.2 | 2 | 2.1 | 1.7 | 1.4 | 0.8 | 3.9 |
| BL-P2044 | 50 | 1.3 | 2.2 | 2.5 | 2.3 | 1.9 | 2.3 | 5.1 |
| | 38 | 0.9 | 1.2 | 1.4 | 1 | 0.8 | 0.6 | 2.4 |
| Amoxicillin + BL-P2013 | 50 | 5.5 | 8.7 | 7.4 | 5.7 | 3.9 | 3.1 | 13.9 |
| | 38 | 1.4 | 2.3 | 2.8 | 2.1 | 1.7 | 1.4 | 4.9 |
| BL-P2049 | 50 | 3.7** | 4.7 | 4.7 | 4.1 | 3.7 | 3.3 | 9.8 |
| | 38 | 4.1 | 4.6 | 3.1 | 2.2 | 1.6 | 1.2 | 6.5 |
| Heta.-Amox. + BL-P2013 | 50 | 3.6** | 7.5 | 8.8 | 6.6 | 5.3 | 3.8 | 15 |
| | 38 | 1.6 | 2.6 | 2.6 | 2.1 | 1.8 | 1.4 | 5 |
| Ampicillin | 50 | 2.2 | 4 | 3.3 | 2.7 | 1.7 | 1.2 | 6.2 |
| Amoxicillin | 50 | 4.2 | 7 | 5 | 3.6 | 2.2 | 1.8 | 9.5 |
| BL-P2013 | 38 | 1.6 | 2.3 | 2.1 | 2 | 1.6 | 1.2 | 4.4 |

*Calculated in terms of ampicillin.
**Calculated in terms of amoxicillin.
Compounds were solubilized in propylene glycol, except for the Hetacillin: BL-P2013 and Heta.-amoxicillin: BL-P2013 mixtures (suspensions).
Assay organism: *E. coli* A9675 for BL-P2013; *B. subtilis* ATCC 6633 for the others.
Data based on 2 tests each for the pro-drugs, and 2 to 5 tests for the others.

TABLE 10

Mouse Blood Levels of Selected Beta-Lactams After Oral Administration with BL-P2013 as Mutual Pro-Drugs or Mixtures
Test Number 2

| Compound | Dose (mg/kg) | Dosage Form[a] | Blood Level (μg/ml) 15 Minutes | 30 | 60 | 90 | 120 | 150 | AUC (μg.h/ml) |
|---|---|---|---|---|---|---|---|---|---|
| BL-P2048 | 50 | PPG | 8[b] | 8.2 | 6.3 | 3.7 | 2.6 | 1.9 | 11.9 |
|  | 50 | TCW ↓ | 5.4[b] | 5.4 | 4.5 | 3.1 | 2.4 | 1.9 | 8.9 |
|  | 38 | PPG | 10 | 9.3 | 4 | 1.3 | 0.9 | 0.6 | 9.2 |
|  | 38 | TCW ↓ | 8.6 | 6.9 | 4.2 | 1.5 | 0.9 | 0.6 | 8.2 |
| Hetacillin + | 50 | PPG ↓ | 1.2[b] | 2.1 | 3 | 3.3 | 3.1 | 2.1 | 6.3 |
|  | 50 | TCW | 1.2[b] | 2.3 | 2.6 | 2.2 | 1.8 | 1.2 | 4.8 |
| BL-P2013 | 38 | PPG ↓ | 1.2 | 2 | 2.1 | 1.7 | 1.4 | 0.8 | 3.9 |
|  | 38 | TCW | 1.7 | 2.2 | 1.7 | 1.1 | 0.9 | 0.6 | 3.3 |
| BL-P2049 | 50 | PPG | 3.7[c] | 4.7 | 4.7 | 4.1 | 3.7 | 3.3 | 9.8 |
|  | 50 | TCW ↓ | 2.9[c] | 4.3 | 3.8 | 3.3 | 2.9 | 2.2 | 8.4 |
|  | 38 | PPG | 4.1 | 4.6 | 3.1 | 2.2 | 1.6 | 1.2 | 6.5 |
|  | 38 | TCW ↓ | 3.1 | 2.7 | 1.2 | 0.8 | 0.6 | <0.5 | 2.9 |
| Heta-Amoxicillin + | 50 | PPG ↓ | 3.6[c] | 7.5 | 8.8 | 6.6 | 5.3 | 3.8 | 15 |
|  | 50 | TCW | 3.6[c] | 6.4 | 7.3 | 5 | 3.4 | 2.2 | 11.7 |
| BL-P2013 | 38 | PPG ↓ | 1.6 | 2.6 | 2.6 | 2.1 | 1.8 | 1.4 | 5 |
|  | 38 | TCW | 1.2 | 1.6 | 1.4 | 0.9 | 0.6 | <0.5 | 2.2 |
| Ampicillin | 50 | PPG | 2.2 | 4 | 3.3 | 2.7 | 1.7 | 1.2 | 6.2 |
|  | 50 | TCW | 2.2 | 3.2 | 2.6 | 1.7 | 0.9 | 0.7 | 3.9 |
| Amoxicillin | 50 | PPG | 4.2 | 7 | 5 | 3.6 | 2.2 | 1.8 | 9.5 |
|  | 50 | TCW | 7.5 | 11 | 9 | 5.7 | 3.1 | 1.9 | 15.4 |
| BL-P2013 | 38 | PPG | 1.6 | 2.3 | 2.1 | 2 | 1.6 | 1.2 | 4.4 |
|  | 38 | TCW | 1.4 | 1.8 | 1.4 | 0.9 | 0.6 | 0.5 | 2.4 |

[a]PPG = Propylene glycol.
TCW = Tween-carboxymethylcellulose-water.
↓ = Drug administered as suspension.
[b]Calculated in terms of ampicillin.
[c]Calculated in terms of amoxicillin.
Assay organism: E. coli A9675 for BL-P2013; B. subtilis ATCC 6633 for the others.
Data based on two tests each for the pro-drugs and 1 to 3 tests for the others.

TABLE 11

Antibacterial Activity of Ceforanide Alone and in Combination with BL-P2013

| Organism | No. of Strains | Ceforanide | MIC (μg/ml)[a] Ceforanide:BL-P2013 1:1 | BL-P2013 |
|---|---|---|---|---|
| S. faecalis | 3 | >125 | >125:>125 | >125 |
| E. aerogenes | 4 | 3.4 | 1.4:1.4 | >125 |
|  | 1 | >125 | 27:27 | 16 |
|  | 5 | >125 | 27:27 | >125 |
| E. cloacae | 1 | 22.6 | 2:2 | >125 |
|  | 14 | >125 | 77:77 | >125 |
|  | 1 | >125 | >125:>125 | >125 |
| Citrobacter sp. | 1 | >125 | 16:16 | 16 |
| C. freundii | 1 | >125 | 63:63 | >125 |
| P. mirabilis | 1 | 0.25 | 0.5:0.5 | >125 |
|  | 3 | 25.4 | 1.6:1.6 | >125 |
| P. vulgaris | 1 | 0.5 | 0.5:0.5 | >125 |
| M. morganii | 9 | 85 | 2.6:2.6 | >125 |
|  | 4 | >125 | 4.8:4.8 | >125 |
|  | 8 | 65 | 1.8:1.8 | >125 |
|  | 8 | >125 | 3.1:3.1 | >125 |
| P. rettgeri | 1 | 0.06 | 0.06:0.06 | >125 |
|  | 1 | 16 | 16:16 | >125 |
| P. stuartii | 1 | 0.35 | 0.5:0.5 | 125 |
|  | 4 | 45 | 27:27 | 125 |
| S. marcescens | 10 | 125 | 51:51 | 125 |
|  | 6 | 125 | 125:125 | 125 |
| P. aeruginosa | 16 | 125 | 125:125 | 125 |

[a]Geometric mean value where applicable.

TABLE 12

Therapeutic Efficacy of β-Lactam Antibiotics and β-Lactamase Inhibitors as Mutual Pro-Drugs or Mixtures After Oral Administration to Mice Experimentally Infected with Different Bacterial Strains

| Organism | | PD$_{50}$/Treatment[a] (mg/kg) | | | | Amoxicillin + BL-P2013 (1:1) |
|---|---|---|---|---|---|---|
| | | BL-P 2048[b] | Hetacillin + BL-P2013 | BL-P 2049[b] | Heta-Amox. + BL-P2013 | |
| E. coli | A-9675 | 49 | 55 | 28 | 16 | 19 |
| E. coli | A21223 | 32 | 21 | 32 | 19 | 21 |
| E. coli | A20649 | 89 | 57 | 43 | 25 | 25 |
| S. aureus | A-9606 | 274 | 121 | >374 | 121 | 114 |
| S. aureus | A20379 | 400 | 200 | >400 | 87 | 200 |

[a]Treatment schedule: Mice were infected i.p. with about 5 × 10$^6$ organisms of E. coli in 4% mucin and 1 × 10$^9$ of S. aureus in 2% mucin. Drugs were administered p.o. at 0 and 2 hour post-challenge.
[b]Mutual Pro-Drugs: BL-P2048 (hetacillin: BL-P2013) and BL-P2049 (heta-amoxicillin: BL-P2013) as well as their respective mixtures were administered in a 50:38 ratio. PD$_{50}$ values are averages of 2 to 3 tests for E. coli and 1 to 2 tests for S. aureus.
PD$_{50}$ values for the amoxicillin: β-lactamase inhibitor mixtures are averages of 1 to 2 tests for E. coli and a single test for S. aureus.

TABLE 13

Therapeutic Efficacy of Mutual Pro-Drugs BL-P2043 and BL-P2044 and Their Components After Oral Administration to Mice Experimentally Infected with a Strain of *E. coli*

| Organism | PD$_{50}$/Treatment[a] (mg/kg) | | | | | | |
|---|---|---|---|---|---|---|---|
| | BL-P 2043[b] | Ampicillin + BL-P2013 | BL-P 2044[b] | Amoxicillin + BL-P2013 | Ampicillin | Amoxicillin | BL-P 2013 |
| *E. coli* A9675 | 44 | 57 | 25 | 25 | >400 | >400 | >50 |

[a]Treatment schedule: Mice were infected i.p. with 8 × 10$^6$ organisms in 4% mucin. Drugs were administered p.o. at 0 and 2 hour post-challenge.
[b]Mutual Pro-Drugs: BL-P2043 (ampicillin:BL-P2013) and BL-P2044 (amoxicillin:BL-P2013) as well as their respective mixtures were administered in a 50:38 ratio. PD$_{50}$ values are based on one test.

The compounds of the present invention are thus useful, given orally and parenterally, for enhancing the effectiveness of β-lactam antibiotics against β-lactamase producing bacteria. On a weight basis, the dosage is from one-fifth to five times, and preferably equal to, that of the β-lactam antibiotics. As an example, the compounds of the present invention as shown above when used in a 1:1 ratio markedly improved the activity of ceforanide and amoxicillin against β-lactamase producing strains of anaerobic Bacteroides such as *B. fragilis*, *B. thetaiotaomicron* and other species of that genus and also against resistant *Staphylococcus aureus*. The compounds of the present invention are given either in admixture with or concomitantly with the β-lactam antibiotic with the dosage within the indicated ratio to the known and customary dosage of the antibiotic.

Thus, the ability of the compounds of the present invention to enhance the effectiveness of a β-lactam antibiotic against certain β-lactamase-producing bacteria makes them valuable for co-administration with certain β-lactam antibiotics in the treatment of bacterial infections in mammals, including man. In the treatment of a bacterial infection, a compound of the present invention can be comingled with the β-lactam antibiotic, and the two agents thereby administered simultaneously. Alternatively, a compound of the present invention can be administered as a separate agent during a course of treatment with a β-lactam antibiotic.

When using a compound of the present invention or salt thereof, to enhance the antibacterial activity of a β-lactam antibiotic, it can be administered alone, or preferably, in formulation with standard pharmaceutical carriers and diluents. A compound of the present invention which is in the acid form or as a pharmaceutically-acceptable salt thereof, can be administered orally or parenterally; a compound of the present invention in the form of an ester which is readily hydrolyzable in vivo, is best administered orally. Parenteral administration includes intramuscular, subcutaneous, intraperitoneal and intravenous administration.

When a compound of the present invention is used in the presence of a carrier or diluent, said carrier or diluent is chosen on the basis of the intended mode of administration. For example, when considering the oral mode of administration, the compound can be used in the form of tablets, capsules, lozenges, troches, powders, syrups, elixirs, aqueous solutions and suspensions, and the like, in accordance with standard pharmaceutical practice.

The proportional ratio of active ingredients to carrier will naturally depend on the chemical nature, solubility, stability and potency of the active ingredients, as well as the dosage contemplated. However, these pharmaceutical compositions will likely contain from about 5% to about 80% of carrier. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols. When aqueous suspensions are required for oral use, the active ingredients are combined with emulsifying and suspending agents. If desired, certain sweetening and/or flavoring agents can be added. For parenteral administration, which includes intramuscular, intraperitoneal, subcutaneous and intravenous use, sterile solutions of the active ingredients are usually prepared, and the pH or the solutions are suitably adjusted and buffered. For intravenous use, the total concentration of solutes should be controlled to render the preparation isotonic.

Although the prescribing physician will ultimately decide the dosage to be used in a human subject, the ratio of the daily dosages of a compound of the present invention, or salt thereof, and the β-lactam antibiotic will normally be in the range from about 1:5 to 5:1, and preferably about 1:1. Additionally, the daily oral dosage of each component will normally be in the range from about 10 to about 200 mg. per kilogram of body weight and the daily parenteral dosage of each component will normally be about 10 to about 100 mg. per kilogram of body weight. These figures are illustrative only, however, and in some cases it may be necessary to use dosages outside these limits.

This invention is capable of industrial application.

I claim:

1. The acid having the formula

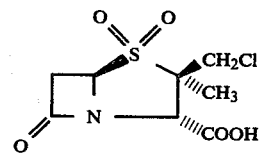

or a pharmaceutically acceptable salt of said acid or an ester of said acid having the formula

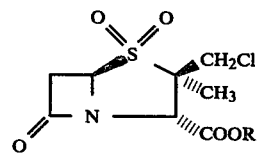

wherein R is phenacyl, acetoxymethyl, pivaloyloxymethyl, α-acetoxyethyl, α-acetoxybenzyl, α-pivaloyloxyethyl, 3-phthalidyl, 5-indanyl, methoxymethyl, benzoyloxymethyl, α-ethylbutyryloxymethyl, propionyloxymethyl, valeryloxymethyl, isobutyryloxymethyl, 6-[(R)-2-amino-2-phenylacetamido]-3,3- dimethyl-7-oxo-4-thia-1-azabicyclo[3.2.0]heptane-2-carbonyloxymethyl or 6-[(R)-2-amino-2-p-hydroxyphenylacetamido]-3,3-dimethyl-7-oxo-4-thia-1-azabicyclo[3.2.0]heptane-2-carbonyloxymethyl.

2. The acid having the formula

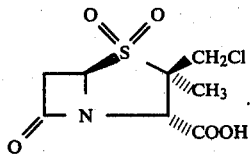

3. A pharmaceutically acceptable salt of the acid of claim 2.
4. The sodium salt of the acid of claim 2.
5. The potassium salt of the acid of claim 2.
6. The ammonium salt of the acid of claim 2.
7. An ester having the formula

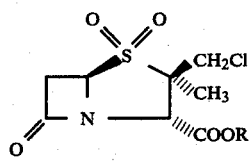

wherein R is phenacyl, acetoxymethyl, pivaloyloxymethyl, α-acetoxyethyl, α-acetoxybenzyl, α-pivaloyloxyethyl, 3-phthalidyl, 5-indanyl, methoxymethyl, benzoyloxymethyl, α-ethylbutyryloxymethyl, propionyloxymethyl, valeryloxymethyl, isobutyryloxymethyl, 6-[(R)-2-amino-2-phenylacetamido]-3,3-dimethyl-7-oxo-4-thia-1-azabicyclo[3.2.0]heptane-2-carbonyloxymethyl or 6-[(R)-2-amino-2-p-hydroxyphenylacetamido]-3,3-dimethyl-7-oxo-4-thia-1-azabicyclo[3.2.0]heptane-2-carbonyloxymethyl.

8. The ester of claim 7 wherein R is acetoxymethyl.
9. The ester of claim 7 wherein R is pivaloyloxymethyl.
10. The ester of claim 7 wherein R is 3-phthalidyl.
11. The ester of claim 7 wherein R is 5-indanyl.
12. The ester of claim 7 wherein R is methoxymethyl.
13. The ester of claim 7 wherein R is phenacyl.
14. The ester of claim 7 wherein R is 6-[(R)-2-amino-2-phenylacetamido]-3,3-dimethyl-7-oxo-4-thia-1-azabicyclo[3.2.0]heptane-2-carbonyloxymethyl.
15. The ester of claim 7 wherein R is 6-[(R)-2-amino-2-p-hydroxyphenylacetamido]-3,3-dimethyl-7-oxo-4-thia-1-azabicyclo[3.2.0]heptane-2-carbonyloxymethyl.
16. The ester having the formula

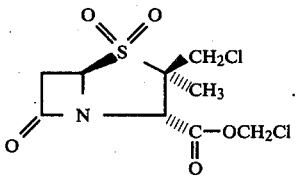

17. The ester having the formula

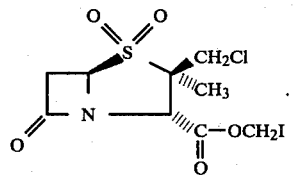

* * * * *